(12) United States Patent
Hage et al.

(10) Patent No.: US 6,720,193 B2
(45) Date of Patent: Apr. 13, 2004

(54) ANALYSIS OF FREE ANALYTE FRACTIONS BY RAPID AFFINITY CHROMATOGRAPHY

(75) Inventors: David S. Hage, Lincoln, NE (US); William A. Clarke, Baltimore, MD (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 09/794,857

(22) Filed: Feb. 27, 2001

(65) Prior Publication Data

US 2002/0151086 A1 Oct. 17, 2002

Related U.S. Application Data

(63) Continuation-in-part of application No. 09/776,800, filed on Feb. 5, 2001.

(51) Int. Cl.$^7$ ............................................. G01N 33/543
(52) U.S. Cl. ..................... 436/518; 435/7.1; 210/656; 436/541; 436/524; 436/161; 530/413
(58) Field of Search .............................. 435/7.1, 288.6; 436/518, 524, 161, 824, 541; 422/70; 210/656, 198.2; 530/412, 413

(56) References Cited

U.S. PATENT DOCUMENTS

| | | | |
|---|---|---|---|
| 4,205,058 A | * 5/1980 | Wagner et al. ................. | 422/61 |
| 4,351,909 A | 9/1982 | Stevens | |
| 4,933,275 A | * 6/1990 | Wands et al. ................. | 435/7.1 |
| 4,937,200 A | 6/1990 | Kumazawa et al. | |
| 5,174,959 A | 12/1992 | Kundu et al. | |
| 5,183,740 A | 2/1993 | Ligler et al. | |
| 5,571,729 A | 11/1996 | Nakamura et al. | |
| 5,595,653 A | 1/1997 | Good et al. | |
| 5,599,677 A | * 2/1997 | Dowell et al. ................ | 435/7.4 |
| 5,605,839 A | 2/1997 | Simpson et al. | |
| 5,800,692 A | 9/1998 | Naylor et al. | |
| 5,863,401 A | * 1/1999 | Chen .......................... | 204/451 |
| 6,080,590 A | * 6/2000 | Van Der Greef et al. ... | 436/536 |
| 6,225,132 B1 | * 5/2001 | Drukier et al. ............. | 436/541 |
| 6,261,848 B1 | * 7/2001 | Anderson et al. ........... | 436/518 |

OTHER PUBLICATIONS

Barre et al., Problems in Therapeutic Drug Monitoring: Free Drug Level Monitoring, *Ther. Drug. Monitoring*, 1988, pp. 133–143, vol. 10, No. 2, Raven Press.

Cassidy et al., Kinetic Chromatographic Sequential Addition Immunoassays Using Protein A Affinity Chromatography, *Anal. Chem.*, Sep. 1992, pp. 1973–1977, vol. 64, Amer. Chem. Society, USA.

Cheng et al., Bovine Serum Albumin Adsorption and Desorption Rates on Solid Surfaces with Varying Surface Properties, *J. Coll. Inter. Sci.*, Jul. 1987, pp. 212–223, vol. 118, No. 1, Academic Press, Inc.

Chignell, Ligand Binding to Plasma Albumin, *Handbook of Biochem. & Mol. Biol.*, 1976, pp. 554–582, 3d Ed., vol. II, CRC PRess, Cleveland, Ohio, USA.

De Alwis et al., Rapid Heterogeneous Competitive Electrochemical Immunoassay for IgG in the Picolmole Range, *Anal. Chem.*, Dec. 1997, pp. 2786–2789, vol. 59, No. 23, Amer. Chem. Society.

Dombrowski et al., Investigation of Anion–Exchange and Immunoaffinity Particle–Loaded Membranes for the Isolation of Charged Organic Analytes from Water, May 1998, pp. 1969–1978 vol. 70, Amer. Chem. Society.

Fernando et al., Investigation of the Kinetic Properties by Particle–Loaded Membranes for Solid Phase Extraction by Forced Flow Planar Chromatography, *Anal. Chem.*, Mar. 1993, pp. 588–595, vol. 65, No. 5, Amer. Chem. Society.

Hage et al., Split–Peak Affinity Chromatographic Studies of the Immobilization–Dependent Adsorption Kinetics of Protein A, *Anal. Chem.*, Feb. 1986, pp. 274–279, vol. 58, Amer. Chem. Society.

Hage et al., Split–Peak Affinity Chromatographic Studies of the Immobilization–Dependent Adsorption Kinetics of Protein A, *Anal. Chem.*, Jan. 1986, pp. 274–279, vol. 58.

Hage et al., Non–Linear Elution Effects in Split–Peak Chromatography, *J. Chromat.*, Feb. 1988, pp. 111–135, vol. 436, No. 2, Elsevier Science Publishers B.V., Amsterdam.

Hage et al., High–Performance Immunoaffinity Chromatography and Chemiluminescent Detection in the Automation of a Parathyroid Hormone Sandwich Immunoassay, *Anal. Chem.*, Mar. 1991, pp. 586–595, vol. 69, Amer. Chem. Society.

Hage et al., Theory of a Sequential Addition Competitive Binding Immunoassay Based on High–Performance Immunoaffinity Chromatography, *Anal. Chem.*, Jun. 1993, pp. 1622–1630, vol. 65, Amer. Chem. Society.

Hage, Immunoassays, *Anal. Chem.*, Jun. 1993, pp. 420R–424R, vol. 65, No. 12, Amer. Chem. Society.

Hage et al., Recent advances in chromatographic and electrophooretic methods for the study of drug–protein interactions, *J. Chromat.*, 1997, pp. 499–525, vol. 699, Elsevier Science.

(List continued on next page.)

*Primary Examiner*—Long V. Le
*Assistant Examiner*—Gary W. Counts
(74) *Attorney, Agent, or Firm*—Stinson Morrison Hecker LLP

(57) ABSTRACT

The invention is generally directed toward an analytical method to determine the concentration of the free analyte fraction in a sample. More particularly, the method encompasses applying a sample comprising a free and bound analyte fraction to an affinity column capable of selectively extracting the free fraction in the millisecond time domain. The signal generated by the free fraction is then quantified by standard analytical detection techniques. The concentration of the free fraction may then be determined by comparison of its signal with that of a calibration curve depicting the signal of known concentration of the same analyte.

24 Claims, 8 Drawing Sheets

OTHER PUBLICATIONS

Hage, Survey of recent advances in analytical applications of immunoaffinity chromatography, *J. Chrom.*, Sep. 1998, pp. 3–28, vol. 715, No. 1, Elsevier Science B.V.

Hage et al., Development of a Theoretical Model for Chromatographic–Based Competitive Binding Immunoassays with Simultaneous Injection of Sample and Label, *Anal. Chem.*, Aug. 1999, pp. 2965–2975, vol. 71, Amer. Chem. Society, USA.

Hage, et al., Development of a Theoretical Model for Chromatographic–Based Competitive Binding Immunoassays with Simultaneous Injection of Sample and Label, *Anal. Chem.*, Aug. 1999, pp. 2965–2975, vol. 71, No. 15, Amer. Chem. Society.

Hagen et al., Membrane approach to solid–phase extractions, *Anal. Chim. ACTA*, 1990, pp. 157–164 vol. 236, Elseivier Science Publishers B.V.

Janis et al., Dual–Column Immunoassays Using Protein G Affinity Chromatography, *Anal. Chem.*, Sep. 1989, pp. 1901–1906, vol. 61, Amer. Chem. Society.

Karamushka et al., Kinetics Of Sorption Immobilization Of Serum Albumin On Silicopolymethyl–siloxane, *Appl. Chem.*, Mar. 1989, pp. 561–564, vol. 62, No. 3, Plenum Publishing Corporation.

Kwong, Free drug measurements: methodology and clinical significance, *Alin. Chim. ACTA*, OCt. 1985, pp. 193–216, vol. 151, Elsevier Science Publishers.

Larsson, High–Performance Liquid Affinity Chromatography, *Enz. Purification & Related Tech.*, 1984, pp. 212–223, vol. 104, Academic Press, Inc.

Levy et al., Utility of Free Level Monitoring of Antiepileptic Drugs, *Epilepsia*, 1985, pp. 199–205, vol. 26, No. 3, Raven Press.

Lok et al., Protein Adsorption on Crosslinked Polydimethylsiloxane Using Total Internal Reflection Fluorescence, Jan. 1983, pp. 104–116, vol. 91, No. 1, Academic Press, Inc.

Loun et al., Chiral Separation Mechanisms in Protein–Based HPLC Colums. 1. Thermodynamic Studies of (R)– and (S)–Warfarin Binding to Immobilized Human Serum Albumin, *Anal. Chem.*, Nov. 1994, pp. 3814–3822, vol. 66, No. 21, Amer. Chem. Society, USA.

Loun et al., Chiral Separation Mechanisms in Protein–Based HPLC Colums. 2. Kinetic Studies of (R)– and (S)–Warfarin Binding to Immobilized Human Serum Albumin, *Anal. Chem.*, Apr. 1996, pp. 1218–1226, vol. 68, No. 7, Amer. Chem. Society, USA.

McElnay et al., Protein Binding Displacement Interactions and their Clinical Importance, *Drugs*, pp. 495–499, vol. 25, No. 5.

Norde et al., Streaming Potential Measurements as a Tool to Study Protein Adsorption Kinetics, *J. Colloid Inter. Sci.*, Oct. 1990, pp. 169–176, vol. 139, No. 1, Academic Press, Inc.

Ohlson et al., High–Performance Liquid Affinity Chromatography: Rapid Immunoanalysis of Transferrin in Serum, *Clin. Chem.*, 1988, pp. 2039–2043, vol. 34, No. 10, Amer. Assoc. for Clin. Chem.

Place et al., Split–Peak Phenomenon in Nonlinear Chromatography. 2. Characterization of the Adsorption Kinetics of Proteins on Reversed–Phase Supports, *Anal. Chem.*, Jul. 1991, pp. 1222–1227, vol. 63, Amer. Chem. Society.

Podgornik et al., High–Performance Membrane Chromatography of Small Molecules, *Anal. Chem.*, Aug. 1999, pp. 2987–2991, vol. 71, No. 15, Amer. Chem. Society.

Pollema et al., Flow Injection Renewable Surface Immunoassay: A New Approach to Immunoanalysis with Fluorescence Detection, *Anal. Chem.*, Jun. 1994, pp. 1825–1831, vol. 66, No. 11, Amer. Chem. Society.

Ramsden et al., Protein Adsorption Kinetics Drastically Altered by Repositioning a Single Charge, *J. Amer. Chem. Soc.*, Aug. 1995, pp. 8511–8516, vol. 117, No. 33, Amer. Chem. Society.

Rollag et al., Analysis of Pesticide Degradation Products by Tandem High–Performance Immunoaffinity Chromatography and Reversed–Phase Liquid Chromatography, *Anal. Chem.*, 1996, pp. 3631–3637, vol. 68, No. 20, Amer. Chem. Society.

Rollag et al., Non–linear elution effects in split–peak chromatography II. Role of ligand heterogeneity in solute binding to columns with adsorption–limited kinetics, *J. Chrom.*, Feb. 1998, pp. 185–198, vol. 795, No. 2.

Shibukawa et al., Analysis Of Warfarin–Albumin Binding By HPLC With Internal–Surface Reversed–Phase Silica Column, *Chem. & Pharm. Bulletin*, May 1988, pp. 1930–1933, vol. 36, No. 5, Pharmaceutical Society of Japan, Japan.

Shibukawa et al., Effect of Protein Binding on High Performance Liquid Chromatography Analysis of Drugs with an Internal–Surface Reversed–Phase Silica Column, *Chem. & Pharm. Bulletin*, May 1989, pp. 1311–1315, vol. 37, No. 5, Pharmaceutical Society of Japan, Japan.

Svensson et al., Free Drug Concentration Monitoring in Clinical Practice Rationale and Current Status, *Clin. Pharmacokinetics*, 1986, pp. 451–469, vol. 11, No. 6.

Thomas et al., Determination of Atrazine in Water Using Tandem High–Performance Immunoaffinity Chromatography and Reversed–Phase Liquid Chromatography, *Anal. Chem.*, pp. 3823–3829, vol. 66, No. 21, Amer. Chem. Society.

Van Dulm et al., The Adsorption of Human Plasma Albumin on Solid Surfaces, with Special Attention to the Kinetic Aspects, *J. Colloid Inter. Sci.*, Jan. 1983, pp. 248–255, vol. 91, No. 1, Academic Press, Inc.

Voegel et al., Adsorption Kinetics of Plasma Proteins Onto Silica, *Coll. & Surf.*, Aug. 1984, pp. 9–19, vol. 10, Elsevier Science Publishers B.V.

Woo et al., Effect of Age and Disease on Two Drug Binding Proteins: Albumin and $\alpha$–1–Acid Glycoprotein, *Clin. Biochem.*, Aug. 1994, pp. 289–292, vol. 27, No. 4.

Young et al., Protein Adsorption on Polymeric Biomaterials, *J. Colloid Inter. Sci.*, Sep. 1983, pp. 246–260, vol. 125, No. 1.

Zhang et al., The Effect of Increasing $\alpha_1$–Acid Glycoprotein Concentration on the Antiviral Efficacy of Human Immunodeficiency Virus Protease Inhibitors, *J. Infect.. Dis.*, Nov. 1999, pp. 1833–1837, vol. 180, No. 5, Infectious Diseases Society of America, USA.

Zhou et al., Membrane Supports as the Stationary Phase in High–Performance Immunoaffinity Chromatography, *Anal. Chem.*, Jan. 1999, pp. 115–118, vol. 71, No. 1, Amer. Chem. Society.

Lindup, W.E., Plasma protein binding of drugs–some basic and clinical aspects, *Progress in Drug Metabolism*, 1987, pp. 141–185, Ch. 4, vol. 10.

Clarke et al., Development of Sandwich HPLC Microcolumns for Analyte Adsorption on the Millisecond Time Scale, Anal. Chem., Mar. 2001, pp. 1366–1373, vol. 73, No. 6, Amer. Chem. Society.

Clarke et al., Analysis of Free Drug Factions by Ultrafast Immunoaffinity Chromatography, Anal. Chem., May 2001, pp. 2157–2164, vol. 73, No. 10, Amer. Chem. Society.

Ageev et al., Derwent Acc. No. 1995–059579. SU 1832194 (Aug. 7, 1993).

* cited by examiner

ANALYSIS OF FREE ANALYTE FRACTIONS BY RAPID AFFINITY CHROMATOGRAPHY

REFERENCE TO RELATED APPLICATIONS

This application is a continuation-in-part of U.S. Ser. No. 09/776,800 filed on Feb. 5, 2001, now pending, which is hereby incorporated by reference in its entirety.

This invention was made with Government support under Grant No. 5 R01 GM044931 awarded by the National Institute of General Medical Sciences. The Government has certain rights in this invention.

FIELD OF THE INVENTION

The invention is directed toward an analytical method to determine the concentration of the free analyte fraction in a sample. More particularly, the method encompasses the use of affinity chromatography to determine the concentration of the free analyte fraction in a sample.

BACKGROUND OF THE INVENTION

Many drugs, hormones, and toxins exist in two distinct forms as they pass through the blood stream: 1) a fraction that is non-covalently bound to proteins or other blood components and 2) a fraction that is non-bound, or free, in solution. The free and bound fractions are present in a dynamic state, in which solutes in one state are continually exchanging with those in the other. Accordingly, in biological systems this process is constant and an equilibrium is formed between the free and bound fractions.

It has long been hypothesized that the free fraction of such substances is the biologically-active form, since it is this form which crosses cell membranes and interacts with cell receptors or other target ligands. Because the free fraction is the biologically-active form, this makes analysis of free fractions of these substances of particular interest in clinical chemistry and pharmaceutical science as a means for controlling and studying their effects within the body.

For many substances it is possible to use their total concentrations in blood or serum as estimates of their free levels by assuming there is a constant relationship between these two types of values. However, there are numerous situations where this approach does not provide meaningful, or even remotely accurate information. For example, after surgery, during malnutrition or pregnancy, and in various disease states (e.g., cancer, renal failure or liver disease) there can be a large fluctuation in the concentration of binding proteins present in blood. This can shift the equilibrium between these proteins and drugs that bind to them and concomitantly cause a change in a drug's free fraction even though its total concentration remains unaffected. Similar shifts in drug-protein binding can occur with age (e.g., in newborns or the elderly) and in situations where several drugs and/or endogenous agents compete for the same binding proteins. A drug with a high total concentration versus its binding proteins also creates problems when trying to estimate the free fraction based upon total protein concentrations since this may result in a non-linear relationship between the drug's total and free levels.

Although several analytical methods have been developed in an attempt to determine the free fraction, all of these methods are plagued with inherent inaccuracies or are lengthy and tedious to perform. Examples of these methods include equilibrium dialysis, ultrafiltration and the use of natural filtrates, such as tears or saliva. A major problem with these techniques is that the analysis often involves the use of an additional binding reagent or separation process that interacts with the free or bound fraction and causes the equilibrium between these fractions to be altered. For example, techniques with long analysis times, on the order of several seconds, results in bias in the measurement process because it allows the release of a significant amount of solutes from the bound fraction which is then detected with the original free fraction. The end result is an error in the apparent concentration of free fraction that is measured. In addition, many of these techniques suffer from non-specific interactions (e.g., binding of drugs to dialysis or filtration membranes), and are limited to only certain types of analytes (as is the case with natural filtrates).

Accordingly, a need exists to determine the free fraction without impacting the equilibrium between the free and bound fractions of the solutes. Equally, a need exists for a method that is highly specific and can be employed to determine the free fraction of a vast number of different substances.

SUMMARY OF THE INVENTION

Among the several aspects of the invention therefore, is provided a method to determine the concentration of a free analyte fraction in a sample, the sample comprising a bound analyte fraction and the free analyte fraction, the method comprising applying the sample to an affinity column wherein the column separates the free analyte fraction from the sample in the millisecond time domain, detection of signal from the free analyte fraction separated from the sample, and determining the concentration of free analyte present in the sample.

In yet another aspect of the invention is provided a method to determine the concentration of a free analyte fraction in a sample, the sample comprising a bound analyte fraction and a free analyte fraction, the method comprising applying the sample to an affinity column, the column separating the sample into the free analyte fraction and the bound analyte fraction in the millisecond time domain wherein the free analyte fraction is adsorbed to the column and the bound analyte fraction passes through the column, applying a series of standards to the affinity column wherein each standard applied comprises a known concentration of the same free analyte present in the sample, the column separating each of the standards into a free fraction and a bound fraction in the millisecond time domain wherein the free fraction is adsorbed to the column and the bound fraction passes through the column, detection of signal from the free analyte fraction separated from the sample in (a) above, detection of signal from the free analyte fraction separated from the standard in (b) above, generating a calibration curve based upon the signal detected in (d) above, the curve comprising a graph of the concentration of free analyte present in each standard versus the signal detected for each concentration, and determining the concentration of the free analyte fraction present in the sample by comparing the signal detected in (c) above with the calibration curve in (e) above.

Yet a further aspect of the invention provides a method to determine the concentration of a free analyte fraction in a sample, the sample comprising a bound analyte fraction and a free analyte fraction, the method comprising applying the sample to an affinity column, the column separating the sample into the free analyte fraction and the bound analyte fraction in the millisecond time domain wherein the free analyte fraction is adsorbed to the column and the bound analyte fraction passes through the column, applying the sample set forth in (a) to an inert control column wherein the free analyte fraction does not adsorb to the column and a total analyte fraction comprising the free analyte fraction and the bound analyte fraction passes through the column, applying a series of standards to the affinity column wherein each standard applied comprises a known concentration of the same analyte present in the sample, the column separating each of the standards into a free fraction and a bound fraction in the millisecond time domain wherein the free fraction is adsorbed to the column and the bound fraction passes through the column, applying the same series of standards set forth in (c) to an inert control column wherein the free analyte fraction does not adsorb to the column and a total analyte fraction comprising the free analyte fraction and the bound analyte fraction passes through the column, detection of signal from the bound analyte fraction of the sample in (a) above, detection of signal from the total analyte fraction of the sample in (b) above, detection of signal from the bound fraction of the standard in (c) above, detection of signal from the total analyte fraction of the standard in (d) above, generating a calibration curve based upon the signal detected in (g) above, the curve comprising a graph of the bound concentration of analyte present in each standard versus the signal detected for each concentration, generating a calibration curve based upon the signal detected in (h) above, the curve comprising a graph of the total concentration of analyte present in each standard versus the signal detected for each concentration, determining the bound analyte fraction in the samples by comparing the signal in (e) above with the calibration curve in (i) above, determining the total analyte fraction in the samples by comparing the signal in (f) above with the calibration curve in (j) above, and determining the concentration of the free analyte fraction present in the sample by subtracting the bound analyte fraction in (k) above from the total analyte fraction in (l) above.

Still another aspect of the invention provides a method to determine the concentration of a free analyte fraction in a sample, the sample comprising a bound analyte fraction and the free analyte fraction, the method comprising applying the sample to an affinity column wherein the column separates the free analyte fraction from the sample in the millisecond time domain, detection of signal from the free analyte fraction separated from the sample and comparing the signal detected in (b) to a standard thereby determining the concentration of free analyte present in the sample.

BRIEF DESCRIPTION OF THE DRAWINGS

These and other features, aspects, and advantages of the present invention will become better understood with regard to the following description, appended claims and accompanying figures where:

Abbreviations and Definitions

Figure 1:
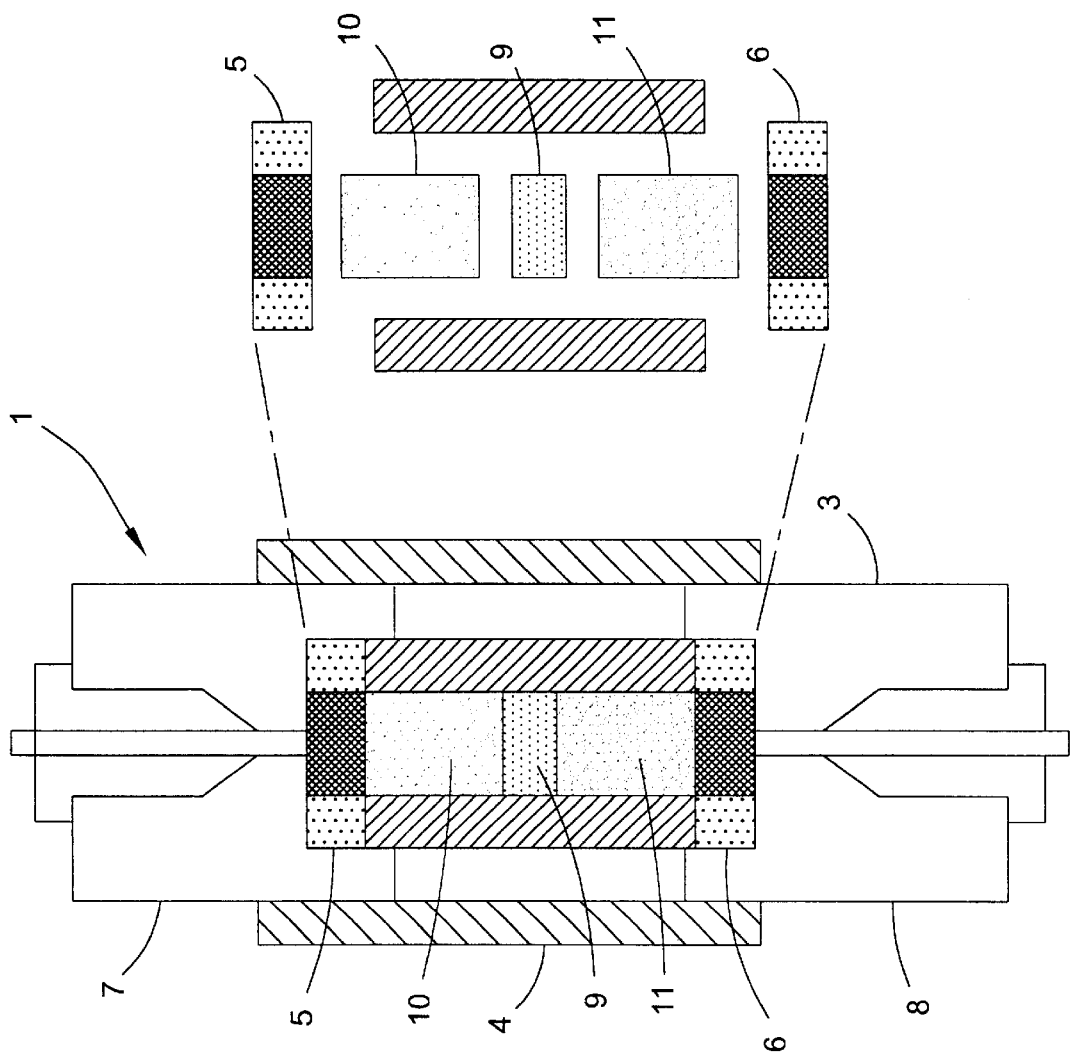
FIG. 1 depicts a drawing of a typical microcolumn that may be employed in the method of the invention.

To facilitate understanding of the invention, a number of terms and abbreviations as used herein are defined below:

"Analyte" or "Target Analyte" are used interchangeably herein, and shall mean the component of the sample that binds to the binding agent present in the active layer of the microcolumn. The analyte will typically comprise the free fraction of a drug, hormone, toxin, metal ion, fatty acid, bilirubin or any other endogenous or exogenous compound. Additionally, the analyte may also comprise any other inorganic or organic compound capable of being separated from the sample, as described herein.

"Binding Agent", as utilized herein, shall mean the agent in the active layer capable of selectively binding the target analyte.

"Binding Compound", as utilized herein, shall mean the compound that the bound fraction binds. Typically, the binding compound comprises a protein, cell or any other endogenous or exogenous compound.

"Bound Fraction" or "Bound Analyte Fraction" are used interchangeably herein, and shall mean the portion of the analyte which is bound to a binding compound.

"Free Fraction" or "Free Analyte Fraction" are used interchangeably herein, and shall mean the portion of the analyte which is not bound to a binding compound.

"Millisecond Time Domain", as utilized herein, shall mean any amount of time less than one second.

"Sandwich microcolumn", as utilized herein, shall mean an embodiment of the invention wherein the microcolumn contains a top inert layer, a bottom inert layer and an active layer between the two inert layers.

"Sample" or "Liquid" are used interchangeably herein and shall mean the mixture applied to the microcolumn containing the analyte. In addition to the analyte, the sample (liquid) generally also contains a loading buffer. Any loading buffer may be employed to the extent that the buffer does not interfere with the separation process. The sample may comprise any mixture with an analyte. Typically, however, the sample will be comprised of a biological fluid such as blood, plasma, urine, cerebrospinal fluid, tissue samples, or intracellular fluid.

"Uniform Manner", as utilized herein, shall mean loading the layers of the microcolumn in a manner such that these layers have a substantially equal distribution of support in both a horizontal and vertical direction.

BSA=Bovine Serum Albumin
FPLC=Fast-Protein Liquid Chromatography
HPLC=High-Performance Liquid Chromatography
Description of the Preferred Embodiments Many compounds, as stated above, exist in two distinct forms as they pass through the blood stream: 1) a fraction that is non-covalently bound to proteins or other binding compounds and 2) a fraction that is non-bound, or free, in solution. The free and bound fractions are present in a dynamic state, in which solutes in one state are continually exchanging with those in the other. Applicants have discovered a method to accurately determine the free analyte fraction of a sample comprising a free analyte fraction and a bound analyte fraction. The method of the present invention employs the use of affinity microcolumns to extract the free fraction of an analyte from the sample in the millisecond time domain. The capability of extracting the free fraction in this time domain allows the free fraction to be separated without impacting the equilibrium between the free and bound fractions. Applicants' discovery, accordingly, circumvents a major problem associated with the long separation times that plague current detection techniques. Upon its separation, the concentration of the free fraction is then determined employing standard analytical methods.

I. Affinity Microcolumn Design and Construction

The method of the present invention employs the use of a microcolumn to separate the free fraction of an analyte from the sample in the millisecond time domain. As utilized herein, the terms "microcolumn" or "column" are used interchangeably and FIG. 1 depicts a typical microcolumn that may be employed in the method of the invention. As shown in FIG. 1, the microcolumn 1 generally has a tubular configuration with a first end 2, a second end 3, a passageway 4 there between, and a retaining means at the first 5 and second ends 6 of the microcolumn 1. However, the microcolumn 1 may comprise any number of different shapes, all of which are embodiments of the present invention. The retaining means 5,6 typically comprises a mesh or small-pore material that acts to hold the support particles within the column while allowing fluid flow there through. The microcolumn 1 may also contain end fittings at the first 7 and second 8 ends of the microcolumn 1 used to connect the column to the chromatographic system. The microcolumn 1 comprises a thin active layer 9 to facilitate separation of the analyte from the sample in the millisecond time scale and typically a single inert layer in one embodiment, to several inert layers in additional embodiments. FIG. 1 illustrates an embodiment with a top inert layer 10 and a bottom inert layer 11.

Figure 2:
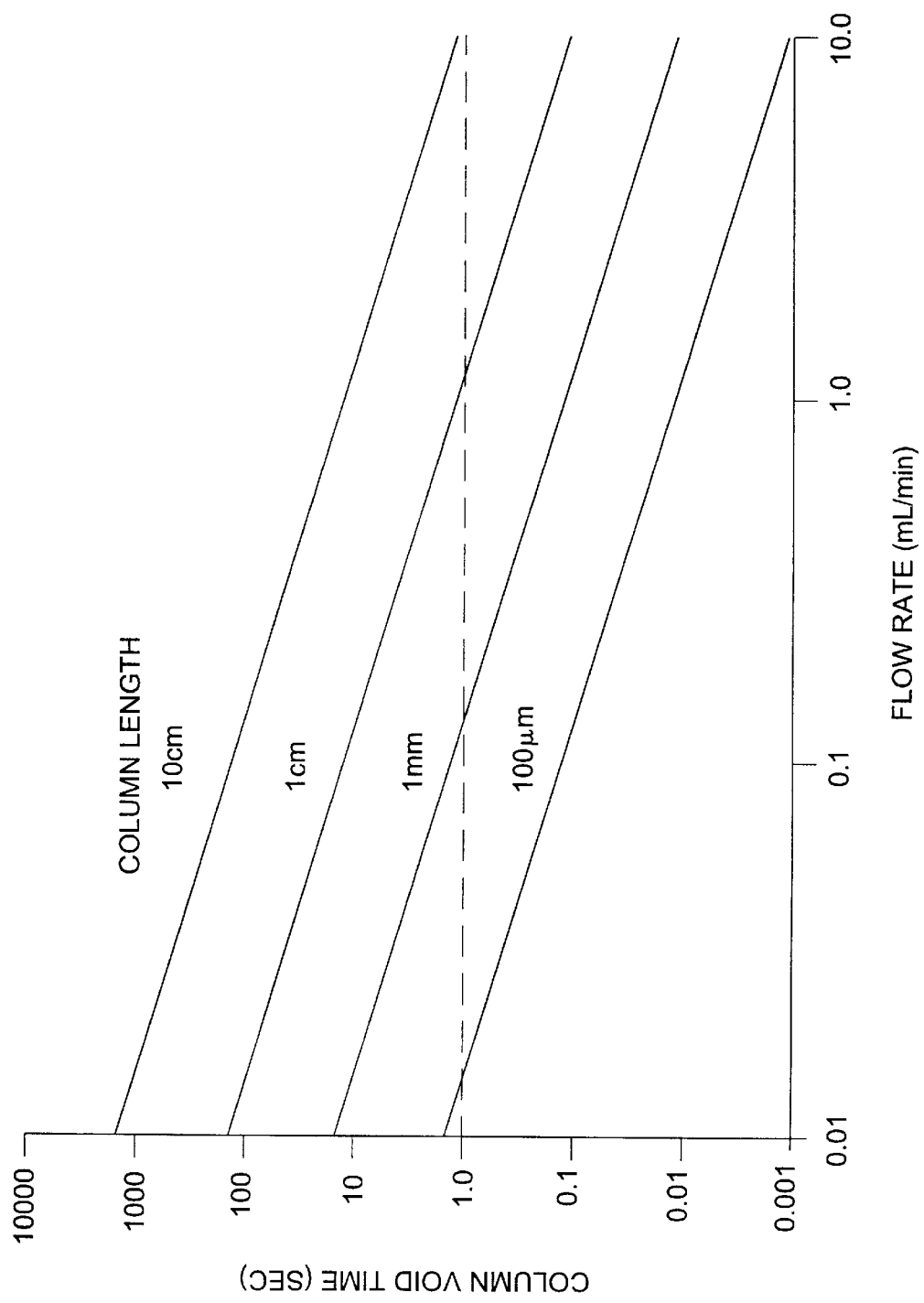
FIG. 2 depicts change in column void time with column length and solvent flow rate for 2 mm ID HPLC columns packed with porous silica. These results assume an overall porosity of 0.80 within the column (i.e., 80% of the column volume is occupied by the mobile phase). Using a column with an inner diameter of 1 mm or 4 mm gives similar results but with the vertical position of the lines in this graph being lowered or raised by 4-fold, respectively.

A salient feature of the current invention is the capability of removing a significant amount of the free fraction of a particular analyte from a sample without release of the analyte from its protein-bound fraction. In order to accomplish this task, as delineated above, the extraction process is preferably accomplished in the millisecond time domain. The microcolumn design described herein is particularly suitable for this application because, due in part to its relatively thin active layer, it can extract the free fraction within this time range. As utilized herein, "length" of a layer means the thickness or width of the layer. As illustrated by FIG. 2 (plot derived by calculation), only columns with active layer lengths in the range of about 100 microns to about 1 millimeter allow separation in the millisecond time domain when employing standard HPLC flow rates of about 0.1 to about 1.0 mL/min. Accordingly, to achieve separation in this time range, the microcolumns employed generally comprise an active layer that may be less than about 10 microns in thickness. Typically, however, the active layer is from about 10 microns to about 1.1 millimeters in thickness and preferably, is not less than approximately 60 microns in thickness. Applicants have found that active layers with these dimensions, depending upon the specific sample applied, are generally capable of extracting an analyte in about 1 to about 500 milliseconds. And, more preferably, in less than about 200 milliseconds.

In addition to rapid extraction of the free fraction, an additional salient feature is the ability of the active layer to bind the target analyte with both a high degree of selectivity and with a relatively high binding affinity. The active layer, therefore, typically is comprised of support particles derivatized with any binding agent possessing selectivity and having a high binding affinity for the target analyte. Preferably, such binding affinity is from about $10^2$ to about $10^6$ $M^{-1}$ or greater. In a preferred embodiment, the binding agents are antibodies raised against the target analyte. The antibodies can be either monoclonal or polyclonal. However, monoclonal antibodies are generally employed in applications where a higher degree of selectivity is desired and polyclonals are more typically utilized in applications where a higher degree of binding 35 affinity is desired. Examples of other suitable binding agents include nucleic acid ligands (e.g. aptamers), synthetic molecular imprints, antibody fragments (e.g. Fab fragments), antibody related molecules (e.g. chimeras or $F_v$, chain fragments), and recombinant proteins that act as antibody mimics. The binding agent, once selected, may be isolated in accordance with any generally known method.

The binding agent can be derivatized to the support particles by any method generally known in the art. However, the method preferably immobilizes the binding agent to the support particle in a manner such that a relatively high percent of the binding agent is active (i.e. binds the target analyte) after the immobilization process. Suitable immobilization methods for protein ligands, for example, include the Schiff base method and the carbonyldiimidazole method. The Schiff base method is generally employed when immobilizing the binding agent through free amine groups.

However, when the binding agent comprises antibodies, applicants have found that a more preferred approach is immobilization through the antibodies' carbohydrate region because this generally results in an active layer with a higher number of active binding sites compared to when immobilization is performed through free amine groups. Any method known in the art for immobilization via carbohydrate regions may be employed.

Additionally, the overall binding capacity of the microcolumn is also an important feature because it impacts both the time and efficiency of extraction by the active layer. The binding capacity of the column, in part, is determined by the number of active binding sites present in the active layer. Preferably, the minimum number of active binding sites in the column comprises a ratio of active binding sites to free analyte not less than about 1:1, and even more preferably, not less than about 10:1. However, still more preferably, support particles in the active layer will be derivatized with the maximum concentration of active binding agent achievable so that the column has the largest binding capacity possible.

The active layer, additionally, may comprise a number of different support particles. The support particles, as detailed above, function primarily as a surface to immobilize the binding agent. The diameter of the particle, however, is an important feature that should be considered because it impacts both the length of the active layer and the amount of binding agent that may be immobilized in the active layer (i.e. binding capacity of the column). Preferably, the particle size is smaller than the length of the desired active layer. Applicants have found that a preferred particle diameter is less than about 10 times to about 20 times the length of the active layer because particles within this size range facilitate uniform packing of the layer by allowing small packing defects to average out and produce a more uniform packing cross-section for the support. In addition, the support particles should be able to tolerate the flow rates and pressures needed in order to obtain the desired sample contact time with the active layer. The properties that affect the pressure and flow rate that may be tolerated by the support particles include the diameter of the particle, the particle's shape and the porosity of the particles. Suitable support particles include porous or nonporous glass, silica and other inorganic supports (e.g., alumina or zirconia), carbohydrate-based supports (e.g., beaded agarose), and polymeric supports (e.g., polymethacryltate or polystyrene based resins); however, one generally skilled in the art of chromatography can select other appropriate support particles.

The microcolumn may comprise a single inert layer or several inert layers, depending upon the application. However, common features shared by all inert layers, irrespective of their number or position within the microcolumn, is that they typically should have no substantial interaction with the target analyte, and should preferably be mechanically stable under the flow rate and pressures employed during the separation process. Preferable materials for construction of the inert layer include diol-bonded silica, diol-bonded glass beads, agarose beads, hydroxylated perfusion media, and glycol coated perfusion media. The various inert layers may be constructed from the same support particles or different support particles. However, it is usually preferred for the sake of convenience in loading the microcolumn that the inert layers comprise the same support particles.

The layers in the microcolumn may comprise either an active layer alone, or an active layer and a single inert layer on top of the active layer (wherein the active layer is in communication with the second end retaining means) such that liquid first passes through the inert layer and then passes through the active layer. The utilization of a single inert layer in this manner is especially suitable for applications where the liquid (containing the sample) is to be applied in only a single direction to the active layer and the column. The inert layer in this application preferably occupies the entire length of the microcolumn between the beginning of the first end of the microcolumn to the beginning of the active layer so that the entire microcolumn is filled with support particles. Applicants have found that having the entire microcolumn filled with support particles increases both the speed and efficiency of separation. Additionally, the inert layer in this application also preferably acts to distribute the injected sample evenly across the diameter of the column before the sample reaches the active layer. This allows for a more uniform application of the sample to the relatively thin active layer.

The layers in the microcolumn may also comprise an active layer sandwiched between a top and a bottom inert layer. As utilized herein, the term "top inert layer" shall mean the layer that liquid first passes through prior to reaching the active layer and "bottom inert layer" shall mean the layer where liquid passes after it exits the active layer. The microcolumn preferably comprises both a top and bottom inert layer for applications where liquid is to be applied in two directions to the active layer and the column. At any given time, the flow of liquid through the column is generally only in a single direction. However, it is sometimes preferable to alternate the flow of liquid through the column in order to help wash out any impurities that may have built up at the top of the column during the application of liquid. The top inert layer in this application serves the same role as discussed above for the application employing a single inert layer e.g. more efficient separation. However, applicants have found that it is preferable to include the bottom inert layer, even in applications where fluid flow is in only a single direction, because its inclusion increases the useful life of the active layer by preventing loss of support particles.

The thickness of the inert layers is not a critical feature and does not affect the time needed to separate the free fraction of an analyte from the sample. In general, as stated above, the top inert layer is preferably the length that remains between the beginning of the column and the beginning of the active layer. And, the bottom inert layer, if it is present, is generally from about 1 to about 5 times the length of the active layer. Typically, the top inert layer is thicker than the bottom inert layer.

The choice of a particular type of housing for the microcolumn is also not a critical facet. The microcolumn housing, however, preferably employs components made of materials that are substantially inert to biological fluids and in particular, substantially inert to the analyte so as not to interfere with the separation process. Accordingly, any material that is substantially inert may be employed to construct the microcolumn. Suitable materials include stainless steel, polypropylene, certain plastics and fused silica.

The dimensions of the microcolumn are also not a critical feature. Any size of microcolumn may be utilized to the extent that the total column length is preferably greater than the length of the active layer. The total column length and diameter also preferably allow the use of sufficiently fast flow rates and pressures to achieve the desired contact time between the sample and the active layer. Preferably, the microcolumn has an internal diameter of about 50 microns to about 2 centimeters and a length of about 0.2 millimeters to about 2 centimeters. In a particularly preferred embodiment, the microcolumn has an internal diameter of about 0.5 to about 2.1 millimeters and a length of about 1 millimeter to about 2 centimeters.

Applicants have found that thin active layers may preferentially be obtained by loading the support particles comprising the layer into the microcolumn via a plurality of injections, as described in detail below (e.g. see FIG. 3). The normal method of loading a column, applying the support particles in one application to the column with the amount of support particles being in excess of that which is needed to fill the column, is sufficient for standard size chromatography columns because due to their size, reliable packing of the support particles may be achieved.

Applicants, however, have found that loading the support particles in a single injection, for columns with dimensions described herein, generally does not result in an active layer capable of consistently achieving separation of an analyte from a sample in the millisecond time scale.

Accordingly, the layers are preferably loaded into the column by a plurality of injections of slurry comprising the support particles. The slurry may be injected into the column employing any apparatus generally known for injecting a slurry into a column, for example, a closed-loop sample application system with either a manual injection valve or an automatic injection system may be utilized. The slurry, in addition to support particles, also preferably comprises a packing solvent or buffer. The packing solvent employed to load the slurry into the column is not a critical feature; however, the solvent preferably will not harm the binding agent present in the active layer. One skilled in the art of chromatography can readily select both an appropriate apparatus to inject the slurry and appropriate packing solvents.

Figure 3:
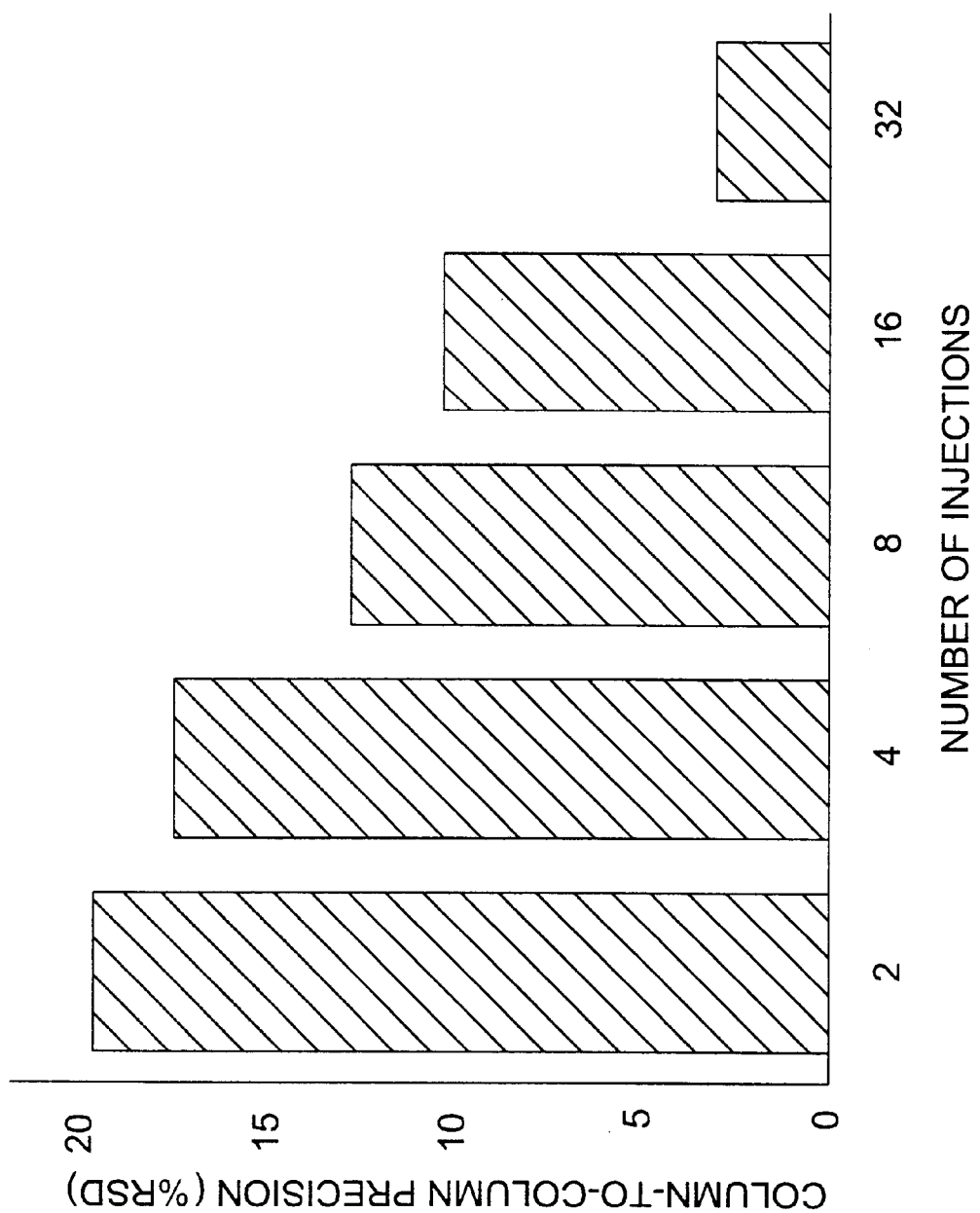
FIG. 3 depicts the reproducibility of stationary phase content in a sandwich microcolumn as a function of the number of injections which were used to apply a fixed amount of an immobilized hemoglobin support to a 2.1 mm ID×620 $\mu$m microcolumn. These results represent the average of triplicate analyses.

Applicants have also found, as illustrated by FIG. 3, employing a larger number of injections and less support per injection, achieves a more controlled delivery of support particles because statistical variations that occur during the delivery of small amounts of support particles to the column are averaged out. This is particularly true as layer thickness decreases. Uniform packing of support particles in the layers, especially the active layer, is preferable because it provides more reproducible results for injected samples by allowing parts of the sample that are injected at different locations along the diameter of the column to achieve consistent sample contact times with the active layer. Accordingly, the number of injections to introduce a layer into the column is generally from about 10 to about 100. More preferably, the number of injections to introduce a layer is from about 30 to about 40 when the layer length is from about 100 to about 500 microns, and is from about 60 to about 80 injections when the layer length is from about 60 to about 100 microns in length.

The slurry density (milligrams of support particles per milliliter of packing solvent), or amount of support particle applied to the column per injection, will vary greatly depending upon the desired thickness of the layer.

Typically, however, the slurry density will be from about 0.1 to about 20 milligrams of support particles per milliliter of packing solvent and more preferably, will be from about 1 to about 5 milligrams of support particles per milliliter of packing solvent. In general, the inert layer(s) and active layer are loaded at approximately the same slurry density. One of ordinary skill in the art can readily determine the appropriate slurry density needed to achieve a layer having a particular thickness when employing a specific number of injections.

The desired slurry density, once selected, is preferably maintained throughout column injection in order to facilitate uniform layer packing. To maintain consistent slurry density, the slurry typically undergoes shaking between injections to ensure that the support particles are uniformly distributed in the slurry. It is also preferable to monitor the turbidity of the slurry at a wavelength of approximately 800 nm to ensure the amount of support particles per milliliter remains constant. Furthermore, typically the slurry density is calculated at numerous points during injection by comparison to slurries of known density employing the same support particles.

Applicants have also found, in addition to loading the support particles by a plurality of injections, that varying the flow rate and pressure during column loading also serves to provide a more uniform and thin active layer. In a particularly preferred application, the pressure and flow rate are increased for a short period of time near the beginning and end of the loading of each layer (as illustrated in Table 1). This increased pressure and flow rate facilitates compression of the layer and distributes the support particles within the layer evenly across the diameter of the column. In a typical column loading procedure, for example, the flow rate of slurry injection into the column is between about 3 mL/min and about 5 mL/min, with the higher flow rate occurring generally at the beginning and end of the loading of each layer.

Additionally, pressure during column loading is typically maintained between about 2000 and about 4000 psi, with a higher pressure preferably occurring at the beginning and end of the loading of each layer. The particular flow rates and pressures utilized to load each layer of the column is not a critical feature and accordingly, may be varied significantly from the general examples provided herein depending upon the particular application.

Table 1 sets forth a general procedure for loading a 1.0 cm immunoaffinity microcolumn comprising an active layer between a top and bottom inert layer. The procedure set forth in Table 1 is for illustrative purposes only and shall not be construed to limit the scope of the present invention as described in greater detail herein.

TABLE 1

General Procedure for Preparing a Microcolumn

| | |
|---|---|
| 1 | Assemble column fittings on the second end of the microcolumn (and retaining means) and attach the microcolumn to the packing apparatus; |
| 2 | Make two particle support slurries in the packing solvent, one consisting of inert support particles, and the other containing the active support particles. For an immunoaffinity microcolumn, the packing solvent employed may be pH 7.0, 0.10 M potassium phosphate buffer and the slurry of the inert support particles typically may contain a diol-bonded material (e.g. 2 mg/mL diol-bonded silica). The second slurry contains the immunoaffinity support particles at a concentration that is determined by utilizing equation 2 or any other generally known method (as set-forth in the examples below) and the desired thickness of the final active layer |
| 3 | Begin flow of the packing solvent through the column. This is generally done at a rate of approximately 3 mL/min for immunoaffinity microcolumns, but is not critical. Make approximately five injections (at 150 uL per injection for a 1.0 cm long column) of the inert support slurry, followed by an increase in flow rate to approximately 5 mL/min for approximately 5 minutes |

TABLE 1-continued

General Procedure for Preparing a Microcolumn

4   Return the flow rate to approximately 3 mL/min and make the required number of injections of the active layer (per equation 2 or any other generally known method). After making these injections, increase the flow rate to approximately 5 mL/min for approximately 5 minutes
5   Return the flow rate to approximately 3 mL/min and make enough injections of the inert support slurry to fill the remainder of the column bed
6   After the column bed has been filled, increase the column backpressure to the desired level, typically about 3000 to about 4000 psi. Allow the column to equilibrate at this pressure for approximately 10 minutes. Gradually release the pressure. Remove the column from the packing apparatus and place a frit (retaining means) and end fitting onto the open end of the column. The column is now ready for use The microcolumn, in addition to its relatively thin active layer, is also generally able to tolerate flow rates and pressures during sample injection that are capable of achieving the desired sample contact time with the active layer. The flow rate and pressure depends not only on the support particles employed in layer construction, but also on the column diameter and upper pressure limit that can be tolerated by the chromatographic system. In general, any flow rate and pressure necessary to achieve the desired residence time and tolerated by the chromatographic system employed is within the scope of the present invention. Typically, however, the microcolumns may be subjected to flow rates of between about 0.01 to about 9.0 mL/min and pressures between about 10 to about 6000 psi. More preferably, the pressure is between about 100 to about 1500 psi.

II. Determination of the Free Analyte Fraction

Encompassed in the method of the invention is a means to determine the concentration of the free analyte fraction in a ample comprising a free fraction and a bound fraction. The method entails generating a calibration curve comprising data obtained by analyzing a series of standards containing a known concentration of the same analyte present in the sample. The concentration of the free analyte present in the sample, as described in detail below, is then determined by comparison to the calibration curve.

Applicants have found that accurately determining the concentration of free analyte in a sample preferably involves the rapid and selective extraction of this fraction from the sample before significant release from its bound fraction. Additionally, applicants have found that this release generally occurs within a few seconds, particularly when the analyte binds a serum protein or other binding compound, such as HSA or alpha 1-acid glycoprotein. The affinity microcolumns described in detail above, therefore, are particularly suited for the method of the invention because they are capable of selectively extracting the free fraction within the millisecond time domain. The bound fraction, on the other hand, does not bind to the affinity column and is therefore present in the liquid fraction that passes through the column.

Accordingly, the method of the invention encompasses applying a sample to the affinity column (described in detail above) under conditions sufficient to bind the free analyte fraction without significant interference from its bound fraction, which passes through the column without adsorbing. The method, irrespective of the embodiment, also entails applying a series of standards to the same affinity column. "Standard" as utilized herein, shall mean a mixture that contains a known concentration of the analyte. The standard will preferably comprise the same analyte as is being detected in the sample and depending upon the embodiment of the invention, may also comprise a binding compound. "Series of Standards" as utilized herein, shall mean applying from about two to about five standards with different analyte concentrations to the column. In another embodiment of the invention, the series of standards may be determined without applying the standards to the column for each application of the method, such as when the calibration curve has been determined previously (from analysis of the same standard in an earlier test) or when the standard comes as a part of a kit. The series of standards will preferably contain concentrations of free analyte that are substantially comparable to the concentration of free analyte expected to be present in the sample.

In accordance with the method of the invention, the concentration of free analyte present in each standard is determined. This concentration may be determined based upon mass or volume measurements in which a known concentration of pure analyte is weighed and placed into a known volume of solution. Equally, a known volume of solution may be diluted or combined with another solution to prepare the final standard solution. In addition to these methods, the concentration may be determined by any means generally known in the art.

Additionally, the sample and standard, irrespective of the embodiment of the invention, are preferably injected onto the column under conditions that optimize a rapid and selective binding of the free analyte to the column. A number of conditions may impact the degree of free analyte binding to the column. These conditions are preferably optimized to achieve a high rate of binding and generally include: 1) an active binding agent in the column that is 35 capable of binding the free analyte, 2) solution conditions (as set forth in more detail below) preferably favorable for binding to occur, 3) the binding capacity of the column is preferably equal to or greater than the concentration of free analyte injected into the column (as discussed above), and 4) the residence time is typically optimized such that the time is preferably long enough that a significant concentration of the free analyte binds to the column and yet, short enough in duration to prevent significant dissociation from the bound fraction. The sample and standards may be applied to the column by any means generally known in the art, such as through the use of an injection valve or autoninjector system.

In addition to the parameters set forth above impacting binding capacity, a number of operating conditions employed during sample and standard injection onto the column are also preferably optimized. One such operating parameter is selection of the loading and elution buffers. The buffers selected preferably mimic the pH and solvent conditions of the sample to ensure that the equilibrium between the free and bound fractions is not disrupted. For example, when a biological sample is being analyzed, any physiological buffer, such as phosphate buffer, may be employed. And, the buffer typically will have a pH of approximately 7.2 to about 7.4 (pH of blood, serum or plasma). The temperature during injection of standard/sample onto the column is also important. Again, the temperature will preferably mimic the natural temperature of the sample to avoid disrupting the binding properties of proteins in the sample prior to their application to the affinity column. Additionally, applicants have found that flow rate during sample injection can dramatically impact both extraction efficiency and dissociation of analyte from the bound fraction. Typically higher flow rates result in less dissociation, while slower flow rates increase extraction efficiency. Therefore, an intermediate flow rate is preferably employed during column injection and one generally skilled in the art of chromatography can readily determine this rate, which will vary depending upon the particular application. Typically, however, the flow rate is from about 0.1 to about 10.0 ml/min, and even more preferably, the flow rate is from about 0.5 to about 1.5 ml/min.

Accordingly, in one embodiment of the invention the concentration of free analyte present in the sample is determined by analyzing data from a series of standards comprising known concentrations of the same free analyte present in the sample without the presence of any binding compounds. In this embodiment, therefore, the concentration of the free fraction is determined by directly analyzing data from the free fraction of the series of standards ("Direct Method"). The sample, as detailed above, is applied to the column employing the same operating parameters as with injection of standard onto the column. The column separates the sample and series of standards into a free fraction and a bound fraction in the millisecond time domain. As detailed above, the free fraction of both the standard and sample is adsorbed to the column, while the bound fraction passes through the column.

The free analyte fraction of both the standard and sample isolated by the column is typically then detected as a signal by any means generally known in the art of analytical chemistry. "Signal" as utilized herein, shall mean the chemical or physical response that allows the analyte to be detected (in either the standard or sample). The signal can either be generated by the analyte itself (e.g. see detection of warfarin in the Example below) or generated by another compound that is linked to the analyte (e.g. the use of a labeled analog of an analyte to allow the unlabeled analyte to be detected). In addition, the signal is specific to the particular detection method employed. The choice of a particular detection method is not critical. However, the detection method employed is preferably the same for both the standard and sample in order to generate a reliable calibration curve. Detection may be performed by either an on-line or off-line method. An "on-line" method, as utilized herein, shall mean a method in which there is a direct coupling between isolation of the free fraction (via affinity chromatography) and its detection such that the isolated fraction is automatically transferred to the detection mechanism through an interface that connects the two systems. An "off-line" method, on the other-hand, as utilized herein, shall mean a method in which the isolated fraction is collected and then manually transferred to the detection mechanism. Suitable detection methods include immunoassay, mass spectrometry, gas chromatography, and detection based upon ultraviolet absorbance, fluorescence detectors, and electrochemical detectors. Preferably, however, the detection technique utilized will comprise an on-line method with direct detection in order to facilitate efficiency of such detection.

The calibration curve can then be generated after the isolation and subsequent detection of signal, as detailed above, of the standard with known concentrations of free analyte. The calibration curve comprises a graph depicting the concentration of free analyte present in each standard versus the signal detected for each concentration.

Additionally, the plot can be generated either manually, with a spreadsheet (e.g. Lotus or Excel) or by employing any computer program generally known in the art for linear or non-linear regression.

The concentration of the free fraction present in the sample can then be readily determined utilizing the calibration curve delineated above by simply comparing the signal detected from the free analyte fraction separated from the sample with the array of signals depicted on the calibration curve. This direct comparison is possible because the curve depicts the signal for known concentrations of the free fraction (generated from the series of standards). Therefore, the concentration of the free fraction of the sample may be determined by comparing its signal to signal depicted in the calibration curve for the standards with known free analyte concentrations.

In yet another embodiment, the concentration of the free analyte fraction of the sample is determined by analyzing data from a series of standards comprising known concentrations of the same free analyte present in the sample and a binding compound. In this embodiment, in contrast to the Direct Method detailed above, the concentration of the free fraction of the sample is determined by analyzing data from the bound fraction and a total fraction (described below) from the series of standards ("Indirect Method"). In this embodiment, similar to the embodiment delineated above, the sample and series of standards are applied to the affinity column employing the same operating parameters. The column separates the sample and series of standards into a free fraction and a bound fraction in the millisecond time domain. Additionally, the free fraction of both the standard and sample is adsorbed to the column while the bound fraction passes through the column. In the Indirect Method, in contrast to the Direct method, the bound fraction of both the sample and series of standards is retained for further analysis in the next step of the method.

However, also in contrast to the Direct Method, the Indirect method employs the use of an additional inert control column. In this embodiment, the same sample and series of standards applied to the affinity column described above are applied to an inert control column. The inert control column comprises a column constructed in all details like the affinity column discussed above except that the support particles in its active layer are not derivatized with a binding agent. For example, the inert control column and affinity column employed in this embodiment are the same size, are constructed from the same materials, and are operated under the same parameters (i.e. pressure and flow rate). However, because the inert control column is not derivatized with binding agent, the free analyte fraction is not separated from either the sample or series of standards. Instead, a total analyte fraction comprising the bound fraction and free fraction pass through the column. The total fraction is retained from both the sample and series of standards for further analysis in the next step of the method.

The signal of the bound fraction of both the sample and series of standards is then detected by any means generally known in the art of analytical chemistry, as described in detail above for the Direct Method. In addition, the signal of the total fraction of both the sample and series of standards is also detected in accordance with the procedures described above for the Direct Method.

In contrast to the Direct Method, the Indirect Method entails generating two calibration curves. The first calibration curve comprises a graph depicting the concentration of analyte present in the bound fraction for each standard versus the signal detected for each concentration. The second calibration curve comprises a graph depicting the concentration of analyte present in the total fraction for each standard versus the signal detected for each concentration. As described above, the calibration curves can be generated either manually, with a spreadsheet (e.g. Lotus or Excel) or by employing any computer program generally known in the art for linear or non-linear regression.

In accordance with the method of the invention, the concentration of the free analyte fraction present in the sample can then be determined utilizing the two calibration curves described above. The concentration of the bound analyte fraction present in the sample can readily be determined by comparing the signal detected for the bound fraction of the sample with the calibration curve depicting the signal detected from the bound fraction of the series of standards with known analyte concentrations. The concentration of the total fraction present in the sample can also be readily determined by comparing the signal detected for the total fraction present in the sample with the calibration curve depicting the signal detected from the total fraction of the series of standards with known analyte concentrations. Finally, per this method, the concentration of free analyte present in the sample can be determined by simply subtracting the concentration of the bound fraction present in the sample from the concentration of the total fraction present in the sample.

The methods of the present invention may be employed to determine the free analyte fraction of any sample comprising a bound and free fraction, to the extent that the free fraction is capable of being separated from the sample, as described herein. A typical application for the method, however, is the clinical analysis of the free fraction of a hormone, drug and other endogenous or exogenous agents present in biological samples. The method may also be employed for the pharmaceutical analysis of free drug levels or drug metabolite levels in biological samples. Equally, the method may be employed in toxicology studies to quantify the free fraction of organic compounds and/or inorganic compounds present in a sample. In a research setting, the method may be utilized to study the mechanism of protein binding processes.

The detailed description set-forth above is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

The examples illustrate the ability of the method of the present invention to detect the free fraction of warfarin from a sample comprising warfarin and human serum albumin ("HSA"). Warfarin is one example of a drug which has significant binding in blood, and is a common anticoagulant used in humans for the treatment and prevention of heart attacks and strokes. It exists in two enantiomeric forms, R-(+)- and S-(−)-warfarin, which are given as a racemic mixture. Both forms have pharmacological activity, but S-warfarin is several times more potent than the R-enantiomer. In the circulation, R- and S-warfarin exist mainly in their bound forms, with most of this binding occurring with the protein HSA. Because of warfarin's pharmaceutical significance, binding affinity for HSA, and stereochemistry, it is an excellent model to illustrate the broad applicability of the method of the current invention.

Materials and Methods

Reagents. The R- and S-warfarin were donated by Dupont Pharmaceuticals (Wilmington, Del.). The polyclonal anti-warfarin antibodies were from Accurate Chemical (Westbury, N.Y.). The HPLC-grade Nucleosil Si-500 and Si-1000 silica (7 µm particle size, 500 Å and 1000 Å pore size) was obtained from Alltech (Deerfield, Ill.). The 7-amino-4-coumarin-3-acetyl hydrazide (AMCA-hydrazide) and reagents for the bicinchoninic acid (BCA) protein assay (Smith, P. K.; Krohn, R. I.; Hermanson, G. T.; Mallia, A. K.; Gartner, F. H.; Provenzano, M. D.; Fujimoto, E. K.; Goeke, N. M.; Olson, B. J.; Klenk, D. C. *Anal. Biochem.* 1985, 150, 76.) were from Pierce (Rockford, Ill.). HSA (Cohn fraction V, 99% pure, fatty acid free) and rabbit immunoglobulin G (IgG) were purchased from Sigma (St. Louis, Mo.). All other chemicals were reagent-grade or better. All aqueous solutions were prepared using deionized water from a Nanopure water system (Barnstead, Dubuque, Iowa).

Apparatus. Samples for the BCA protein assay were analyzed using a Shimadzu UV160U absorbance spectrophotometer (Kyoto, Japan). Immunoaffinity columns were packed using a modified N60 injection valve from Valco (Houston, Tex.) and a CM3000 HPLC pump from LDC Analytical (Riviera Beach, Fla.). The final chromatographic system used in the analysis of free and bound warfarin consisted of one anti-warfarin immunoaffinity microcolumn (prepared as described later) in series with two 5 cm×2.1 mm ID Pinkerton GFF II internal surface reversed-phase (ISRP) columns from Regis Technologies (Morton Grove, Ill.). Detection in the chromatographic system was performed by a Shimadzu RF-535 fluorescence monitor. Samples were injected by an AS3000 autosampler from Thermoseparations (Schaumberg, Ill.). The application and elution buffers for the immunoaffinity column were delivered using PU-980 HPLC pumps from Jasco (St. Louis, Mo.). A LABPro automated six-port valve from Rheodyne (Cotati, Calif.) was used to switch between these buffers. An organic modifier for displacement of the HSA-bound warfarin was introduced to the effluent of the immunoaffinity column through the use of a post-column mixing tee and a CM3200 pump from LDC Analytical. The chromatograms were collected on a 300 MHZ Pentium computer from TCE (Hoffman Estates, Ill.) with Winner-on-Windows software from Thermoseparations. The temperature of the system was controlled using a VWRbrand 13L immersion circulating water bath from VWR Scientific (West Chester, Pa.).

Preparation of Immunoextraction Column. Antibodies were purified using AMCA-hydrazide as an affinity ligand. AMCA is a coumarin derivative that is similar in structure to warfarin. It was used here to isolate anti-warfarin antibodies from their corresponding antiserum. The AMCA-hydrazide was coupled to Nucleosil Si-1000 silica in a manner similar to that reported for the synthesis of dihydrazide-activated silica (Ruhn, P. F.; Garver, S.; Hage, D. S. *J. Chromatogr. A* 1994, 669, 9.). The anti-warfarin antibodies were isolated with this support by incubating one milliliter of anti-warfarin antiserum with 300 mg of the AMCA silica for two hours at room temperature. After 15 incubation, the samples were centrifuged and the supernatant was removed. The support was then washed with pH 2.5, 0.10 M potassium phosphate buffer for 10 min, followed by a second centrifugation step. This second supernatant (containing purified anti-warfarin antibodies) was then collected, adjusted to pH 7.0 with a small concentration of 1.0 M sodium hydroxide, and stored at 4° C. until further use.

Diol-bonded Nucleosil Si-500 silica was prepared as described previously (Ruhn, P. F.; Garver, S.; Hage, D. S. *J. Chromatogr. A* 1994, 669, 9.). The diol coverage of this support was 127±4 (1 SD) μmol/g of silica, as determined in replicate by an iodometric capillary electrophoresis assay. The purified anti-warfarin antibodies were immobilized to this diol-bonded silica by the Schiff base method (Larsson, P.-O. *Methods Enzymol.* 1984, 104, 2121.). The protein content of the resulting immunoaffinity support was determined by a BCA assay to be 2.05±0.05 mg antibodies/g silica (or 14 nmol/g), using rabbit IgG as the standard and diol-bonded silica as the blank.

The anti-warfarin immunoaffinity support was used to pack a sandwich microcolumn, as described herein. This column had an inner diameter of 2.1 mm and a total length of 1.0 cm, with a 1.1 mm portion containing the immunoaffinity support and the remainder containing an inert layer of diol-bonded silica. The immunoaffinity layer was placed within this column by making thirty-two 250 μL injections of a 0.3 mg/mL slurry of the anti-warfarin support in pH 7.0, 0.10 M phosphate buffer. The remainder of the column was filled in a similar manner with diol-bonded Nucleosil 500.

Chromatographic Studies. The extraction studies were performed by making 20 μL injections of $0.8-5\times10^{-7}$ M warfarin at flow rates ranging from 0.5 to 3.0 mL/min. Five replicate injections were made at each flow rate using microcolumns that contained the immunoaffinity support or only diol-bonded silica. The non-retained peaks observed with the immunoaffinity column were compared to those seen on the diol column to determine the relative concentration of warfarin that had been removed by the immobilized antibodies. The application buffer in these studies was pH 7.0, 0.10 M potassium phosphate and the elution buffer was pH 2.5, 0.10 M potassium phosphate. Between injections, the immunoaffinity column was washed for 5 min with the elution buffer at 1.0 mL/min and was allowed to regenerate for 10 min in the application buffer at 1.0 mL/min.

The separation of HSA and HSA-bound warfarin was studied by injecting 20 μL of warfarin/HSA mixtures onto a diol microcolumn that was in series with two ISRP columns. The samples in this study contained $0-3.5\times10^{-5}$ M warfarin and 3 mg/mL ($4.5\times10^{-5}$ M) HSA in pH 7.0, 0.10 M phosphate buffer. These samples were injected at 1.0 mL/min in the presence of the pH 7.0 application buffer. A separate solvent stream was introduced directly after the microcolumn using a three-way mixing tee. In the final optimized system, this second solvent stream contained 7.5% 1-propanol in pH 7.0, 0.10 M phosphate buffer and was added at a flow rate of 0.2 mL/min to induce dissociation of HSA-bound warfarin. The same chromatographic system was used to determine the concentration of free warfarin in warfarin/HSA mixtures by replacing the diol column with the immunoaffinity microcolumn. A series of twenty replicate injections were made in this experiment using samples that contained well-defined concentrations of R- or S-warfarin and HSA. The non-retained peak areas for the warfarin in these samples were then compared to the areas obtained for warfarin/HSA standards with the diol column.

Computer Simulations. The simulations of warfarin extraction and dissociation were performed on an IBM-compatible computer using programs written in Turbo C++ (Borland International, Scotts Valley, Calif.). This was accomplished by using a grid propagation algorithm that has previously been used to examine the adsorption of analytes to immobilized antibodies and similar ligands in affinity columns. This algorithm was modified to include the reversible binding of an analyte to an agent in the mobile phase. In this method, the column was divided into a large number of slices of equal width. As an analyte moved through this column, its binding to the immobilized ligand and soluble agent in each slice was described by using mass balance and the differential equations for the rates of these reactions. This system of equations was solved for that particular slice and interval of time by using a fourth-order Runga-Kutta method (Margenau, H.; Mosely, G. M. *The Mathematics of Physics and Chemistry*; Van Nostrand; Princeton, 1956.). Flow through the column was simulated after each iteration by taking the compounds that remained in the mobile phase and moving these onto the next slice. The process of distributing and moving the analytes was repeated until all of the analyte had either bound to the immobilized ligand or had left the column. The relative concentration of analyte that had adsorbed to the column was then calculated, thus providing the retained fraction. Convergence of these results was tested by performing a series of related simulations in which the column was divided into an increasing number of slices but with a decreasing concentration of time being used per iteration in each slice. This gave a maximum estimated error of less than 0.2% in the calculated concentration of retained analyte.

EXAMPLE 1

Initial Selection of Conditions for Free Drug Extractions

Previous reports have measured the equilibrium and rate constants for the binding and dissociation of R- and S-warfarin with HSA under a variety of conditions (Loun, B.; Hage, D. S. *Anal. Chem.* 1994, 66, 3814 and Loun, B.; Hage, D. S. *Anal. Chem.* 1996, 68, 1218.). Based on this information, it was possible to estimate the time needed to remove the free fraction of warfarin from a warfarin/HSA mixture without having this fraction contain a significant concentration of warfarin that had been released from its protein-bound form. Some plots that were used to study the extent of this dissociation process are shown in FIG. 4 These particular results were calculated for S-warfarin at 25° C. under conditions similar to those used in this study.

This type of plot was also generated for R-warfarin, which has a slightly faster rate of dissociation from HSA under the given experimental conditions.

The model used in FIG. 4 assumes 1) that there is an instantaneous removal of all free warfarin from the initial sample, 2) that any warfarin which is later released from its complex with HSA will bind immediately to the extraction column, and 3) that the concentration of extracted warfarin is much smaller than the binding capacity of the column. Based on this model, it was found that roughly 75% of the S-warfarin that was originally bound to HSA would be released from this protein and adsorbed to the extraction column within 10 s. This indicated that ordinary immunoaffinity extractions, which often take several minutes to perform, (Hage, D. S. J. Chromatogr. B 1998, 715, 3.) would be much too long for separating the free and bound fractions of S-warfarin. An expanded view of this dissociation process, illustrated in FIG. 4 (b), indicated that extraction times of only a few hundred milliseconds would be required to isolate the free fraction of S-warfarin while avoiding any appreciable contamination by warfarin that had been later released from HSA. The same conclusion was reached in calculations that were performed for R-warfarin.

Figure 4A:
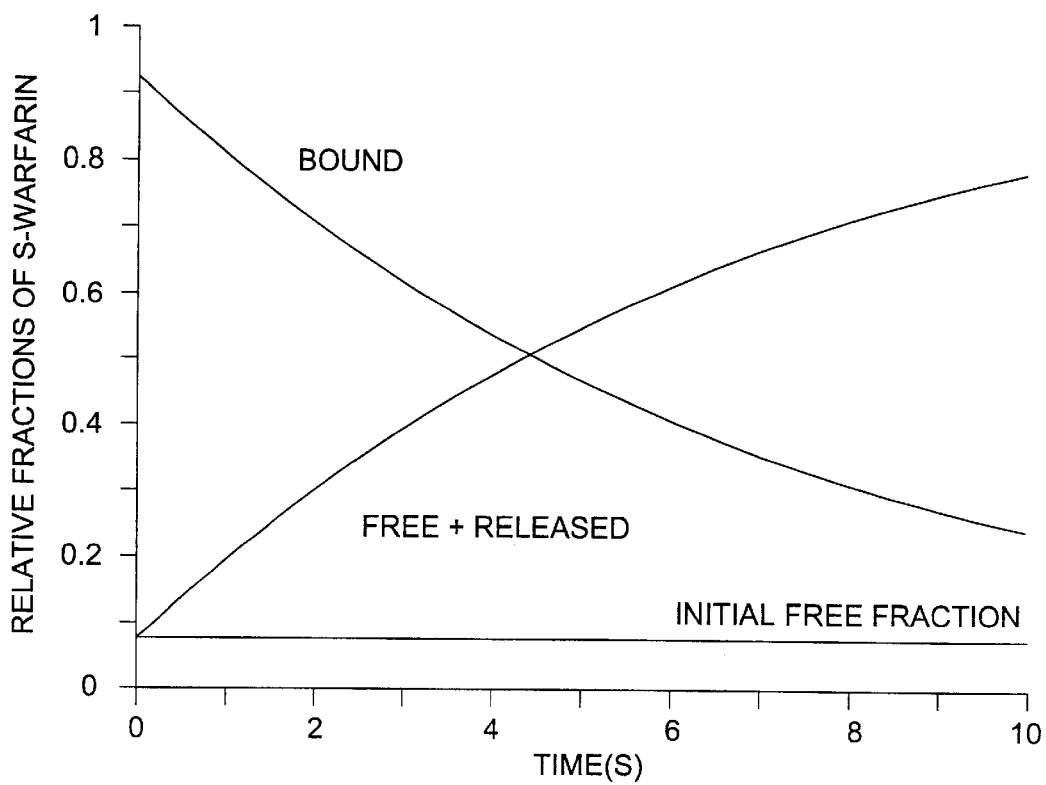
FIG. 4 depicts release of protein-bound S-warfarin following the instantaneous removal of this drug's free fraction from an equilibrium mixture of S-warfarin and HSA. The graph in (a) shows the progression of this reaction over ten seconds, while the plot in (b) shows an expanded view on the sub-second time scale. These graphs were generated for a starting mixture that contained $4.56 \times 10^{-5}$ M HSA and $1.1 \times 10^{-5}$ M S-warfarin at 25° C. An equilibrium constant of $3.4 \times 10^5$ M$^{-1}$ was used to determine the initial amount of free warfarin in this sample. A first-order rate constant of 0.14 s$^{-1}$ was used to describe the dissociation of S-warfarin from HSA.
Figure 4B:
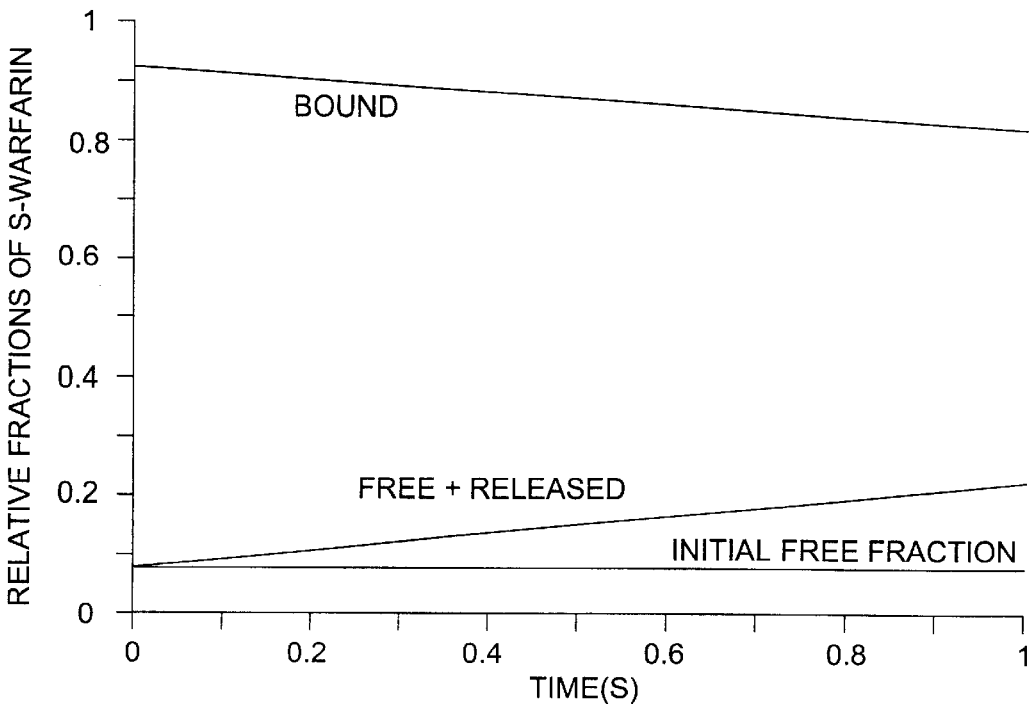

Although it was useful in FIG. 4 to assume that there was an excess of binding sites in the column and that there was immediate removal of any non-complexed warfarin from solution, this does represent a worst-case scenario and probably resulted in estimates for the usable extraction times which were smaller than those that might be possible in practice. For instance, either the presence of a finite number of binding sites in the column or a finite rate of adsorption for the non-complexed warfarin would reduce any perturbation of the HSA-bound fraction of warfarin as this passes through the immunoaffinity column. The same thing would happen if the warfarin in solution were allowed to reassociate with HSA instead of being removed by the column. The effects of eliminating these assumptions will be considered through the use of computer simulations. However, the model used in FIG. 4 was still found to be a good starting point for estimating the conditions needed in an immunoaffinity column for isolating a drug's free fraction.

Design of Immunoaffinity Column. Based on FIG. 4, an extraction time of less than 200 ms was set as the initial goal for the removal of free warfarin from warfarin/HSA mixtures at room temperature. Under these conditions, an error of less than 20–40% in the measured free fractions of R- and S-warfarin was expected due to the dissociation of their protein-bound fractions. In order to work within this time frame it was necessary to prepare a column that was 35 capable of operating in the millisecond time domain. This was accomplished by using a sandwich microcolumn that was prepared as described herein. This consisted of a 2.1 mm ID ×1.0 cm tube that was packed with a 1.1 mm thick layer of a support that contained immobilized anti-warfarin antibodies. The remainder of the column was filled with diol-bonded silica. The purpose of the immunoaffinity support was to extract warfarin from samples, while the diol-bonded silica was used to hold the immunoaffinity support in place and to provide uniform sample application to this layer.

In this type of column the actual time over which free drug extraction and sample perturbation takes place is represented by the time during which any given part of the sample passes through the immunaffinity layer. For instance, an effective extraction time of 200 ms or less would be obtained by using a flow rate of at least 0.9 mL/min on a 2.1 mm ID column that contains a 1.1 mm layer of an immunoaffinity support. This is well within the range of usable conditions for these columns, which have been operated at flow rates as high as 9–10 mL/min.

The binding capacity of the immunoaffinity columns also had to be considered to ensure that overloading did not occur when warfarin samples were injected onto these columns. The concentration of warfarin binding sites in one anti-warfarin microcolumn was estimated to be 50 pmol. Although this is a relatively small concentration of ligand, it is still three-to-five times larger than the concentration of free warfarin that was applied in any sample, thus indicating that these columns did have a sufficient binding capacity for this present study. This was confirmed experimentally by measuring the maximum concentration of warfarin that could bind to the microcolumn as the concentration of injected warfarin was varied.

Figure 5:
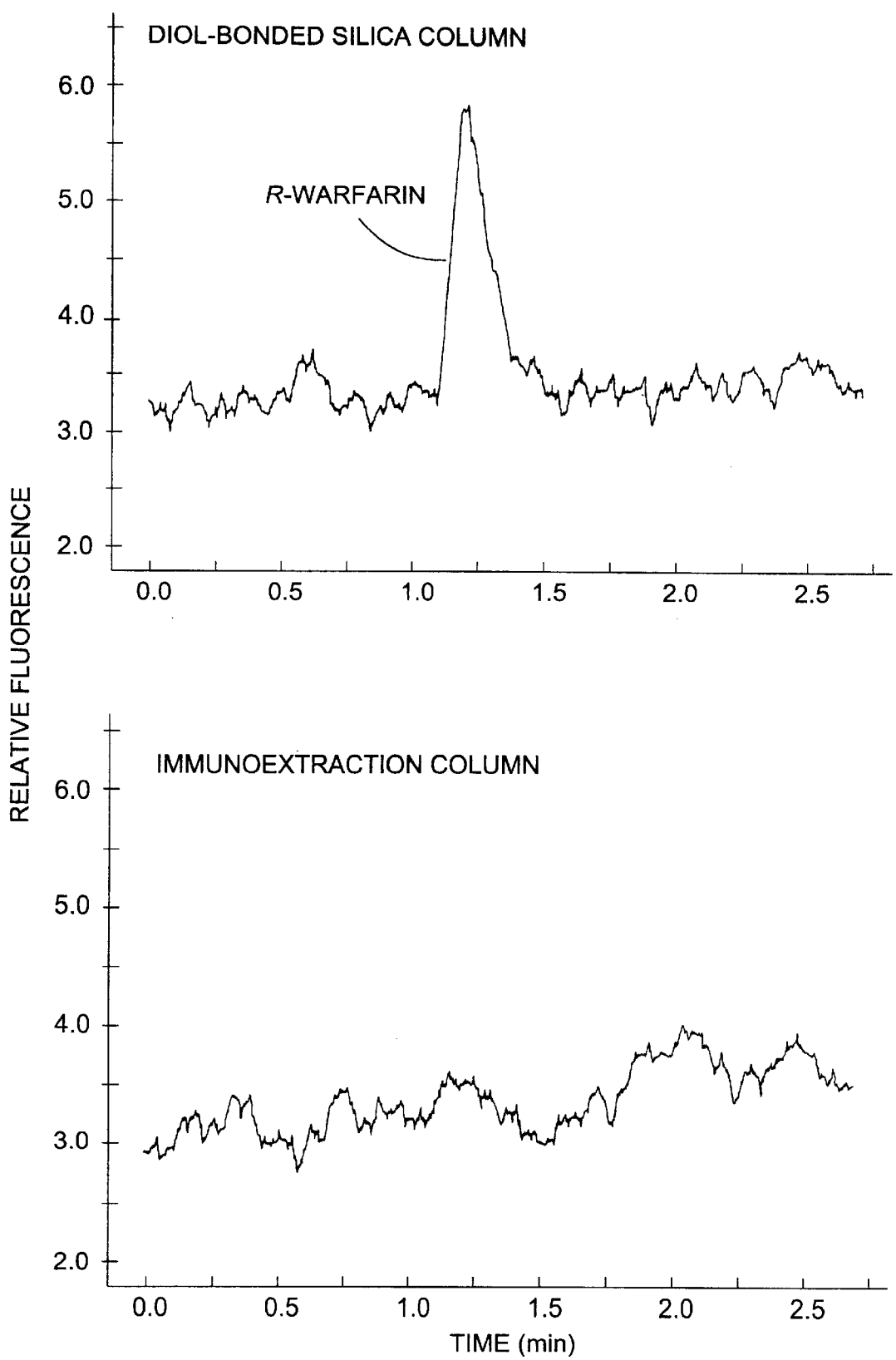
FIG. 5 depicts chromatograms for the injection of a 20 $\mu$L sample of $8 \times 10^{-7}$ M R-warfarin onto (a) a diol-bonded silica column and (b) an anti-warfarin immunoaffinity column at a flow rate of 3.0 mL/min (effective column residence time, 60 ms). Other experimental conditions are provided in the Materials and Methods of the Example section.

One question that remained was whether this type of microcolumn could be used to extract warfarin on the millisecond time scale. This was tested by injecting samples that contained only R- or S-warfarin at various flow rates. The results obtained on the immunoaffinity column were then compared to those observed for the same samples and flow rates on an inert control column. FIG. 5 shows an example of such a study. It was found that in 120 ms there was 95% extraction of a $5 \times 10^{-7}$ M warfarin sample (i.e., a concentration corresponding to the free warfarin content expected for the warfarin/HSA mixtures examined later in this report). At even lower concentrations, such as the $8 \times 10^{-8}$ M warfarin sample shown in FIG. 5, essentially complete extraction was possible in 60 ms. Thus, it was concluded that immunoaffinity microcolumns could be used to extract warfarin on the same time scale that was needed for separating warfarin's free and protein-bound fractions.

EXAMPLE 2

Separation of Free and Bound Warfarin Fractions.

The next section of this study began to examine the use of an immunoaffinity microcolumn to measure the free drug fractions of mixtures that contained known concentrations of HSA and R- or S-warfarin. This was to be done by monitoring the fluorescence of any warfarin that passed non-retained through the immunoaffinity column. One difficulty with this approach is that warfarin has a significant change in its degree of fluorescence when it is in solution versus bound to HSA. This, plus the inherent fluorescence of HSA, created a problem in detection because the non-retained samples were expected to contain a mixture of HSA, HSA-bound warfarin, and warfarin that had dissociated from HSA.

Figure 6:
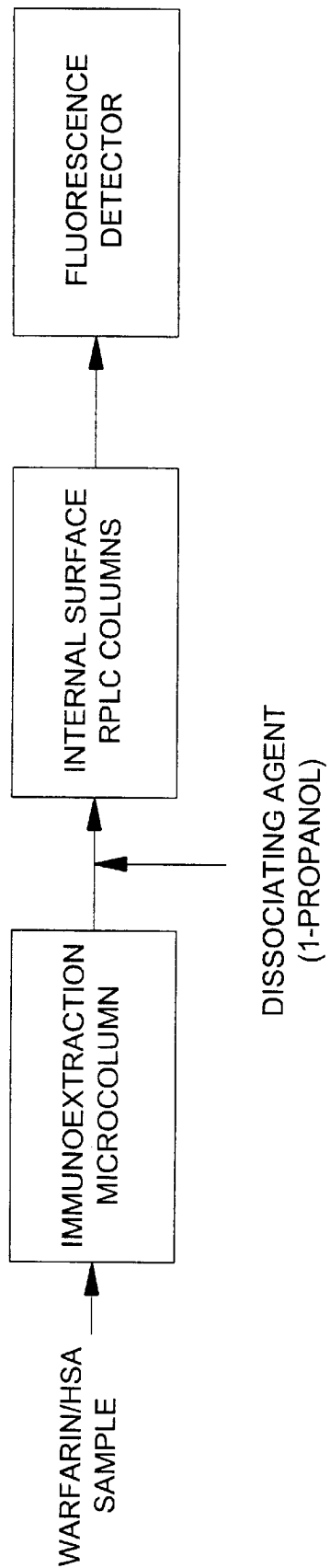
FIG. 6 depicts a schematic of a chromatographic system for the extraction and measurement of free and protein-bound warfarin. Details on the construction of this system can be found in the Materials and Methods of the Example section.

The approach used to overcome this problem was to pass the non-retained sample peaks through a series of ISRP (internal surface reversed-phase) columns. This was done by using the system illustrated in FIG. 6. Although all of the bound warfarin would eventually be released from HSA in such a system, a dissociating agent (1-propanol) was added to the microcolumn effluent to increase the rate of this process.

The 1-propanol also acted as an organic modifier to aid in the elution of components on the ISRP columns.

Figure 7:
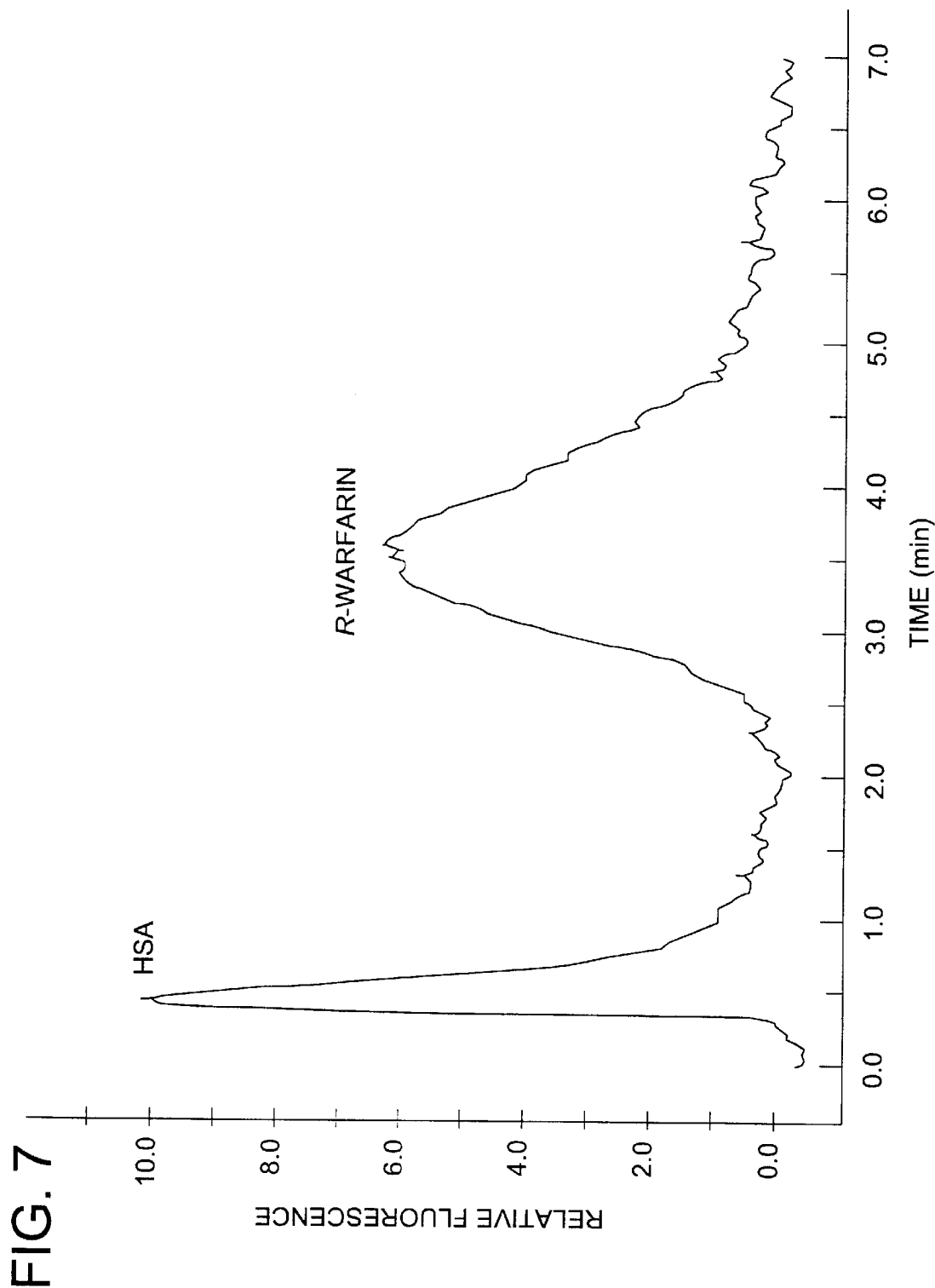
FIG. 7 depicts a chromatogram for separation of HSA from R-warfarin after the passage of these compounds as a mixture through an anti-warfarin immunoaffinity microcolumn. The initial sample contained $1.1 \times 10^{-5}$ M R-warfarin and $4.5 \times 10^{-5}$ M HSA. Other conditions are provided in the text.

A typical chromatogram for this system is shown in FIG. 7. As demonstrated in earlier studies, proteins like HSA are too large to fit in the pores of an ISRP column and will elute in its excluded volume. However, smaller molecules like warfarin can enter these pores and interact with the hydrophobic phase that is located there. This will cause these molecules to be retained and to elute after proteins from these columns. In the case of this study, the second peak was much broader than the first since it was produced by warfarin that entered the pores at different points along the column as it began to undergo dissociation from HSA.

ISRP columns have been used alone for the analysis of free and bound warfarin in the presence of bovine serum albumin. In these earlier studies, the free warfarin was retained at the beginning of the ISRP column, while the bound fraction underwent dissociation from albumin and was retained further downstream. It was shown that this resulted in three overlapping peaks: the first representing the non-retained protein, the second corresponding to warfarin which dissociated from this protein, and the third (and slowest eluting peak) representing warfarin's initial free fraction. It is important to note in this present study that the free warfarin peak was not observed on the ISRP column when the samples had previously passed through the immunoaffinity column. This occurred because the free fraction had now been removed from these samples. This allowed a much cleaner separation to be obtained between the bound and free fractions of this drug and its binding proteins than was reported when using only ISRP supports.

Various factors were adjusted to obtain the separation shown in FIG. 7. The rate of warfarin dissociation from HSA was increased in the ISRP column by adding 1-propanol to the effluent of the immunoaffinity column. This resulted in a sharper peak for the bound warfarin fraction since it was now released over a shorter distance within the ISRP column.

A 7.5% solution of 1-propanol was found to be optimum for this purpose since it allowed complete dissociation of warfarin from HSA in a reasonable time while still providing a large enough difference in retention for their separation. A longer length for the ISRP support was also employed (going from one 5 cm long column to two 5 cm columns) to increase the efficiency of this system and its ability to resolve the HSA and bound warfarin peaks. The result was a separation in which baseline resolution was obtained within 5 min of sample injection.

One small problem in using multiple ISRP columns was that this increased the back pressure of the overall chromatographic system. This placed a limit on the maximum flow rate and minimum sample residence time that could be used with the immunoaffinity microcolumn. As a compromise between extraction time, sample throughput and these pressure limitations, an injection flow rate of 1.0 mL/min was chosen for the final system. This gave a residence time of 180 ms for samples in the immunoaffinity column. As noted earlier, this concentration of time not only was sufficient to allow the quantitative extraction of warfarin, but it also fell within the range of 200 ms or less that was initially selected for use in separating warfarin's free and bound fractions.

EXAMPLE 3

Analysis of Free Warfarin Fractions

The fourth phase of this study used the immunoaffinity and ISRP system to measure the concentration of free warfarin in known mixtures of warfarin and HSA. To quantitate the free warfarin in these samples, standard curves were first prepared in which various concentrations of R- or S-warfarin were mixed with HSA. These mixtures were then injected onto the system shown in FIG. 6, with diol-bonded silica being used in place of the immunoaffinity support in the extraction column. The area of the warfarin that eluted from the ISRP columns (now corresponding to both the bound and free warfarin fractions) was measured and plotted as a function of the total warfarin concentration in the sample. Both R- and S-warfarin gave linear responses in these plots with correlation coefficients of 0.9991–0.9993 for ten samples that contained warfarin concentrations of $0-1.7 \times 10^{-5}$ M. The lower limit of detection of this method for these enantiomers was about $0.5-1 \times 10^{-8}$ M (S/N=2). This detection limit was 50 to 100-fold smaller than the free warfarin concentrations which were measured in this study.

The warfarin and HSA mixtures that were being used as test samples were now injected onto the same system in the presence of 1) a microcolumn that contained only diol-bonded silica or 2) the immunoaffinity column that had previously been developed for the millisecond-scale extraction of warfarin. The peak area obtained with the diol column allowed the total concentration of warfarin in the sample to be determined. The area measured after extraction by the immunoaffinity column allowed the concentration of bound warfarin to be estimated. By combining these two values it was then possible to calculate the concentration of free warfarin in the sample.

This approach was tested by injecting a set of samples that contained $0.95-1.10 \times 10^{-5}$ M R- or S-warfarin and $4.5 \times 10^{-5}$ M HSA. Both the R- and S-warfarin samples were injected twenty times onto the diol column and immunoaffinity column. This gave relative standard deviations of ±4–6% for their measured peak areas on the ISRP system. The free fractions that were obtained for these samples are shown in Table 2, below. For R-warfarin, the free fraction was determined to be 11.8±0.6% at 25° C. (or a bound fraction of 88.2%), while for S-warfarin the free fraction was 5.9±0.2% (or 94.1% bound).

TABLE 2

Measured and predicted free fractions for R- and S-warfarin in samples containing known mixtures of warfarin and HSA[a]

| Compound | Measured Free Fraction | Predicted free Fraction[b] |
|---|---|---|
| R-Warfarin | 11.8 (±0.6) % | 10 (±2) % |
| S-Warfarin | 5.9 (±0.2) % | 7 (±1) % |

[a]All values shown in parentheses represent a range of ±1 SD.
[b]The predicted free fractions were determined by using the known compositions of the samples and equilibrium constants which have previously been measured for the binding of warfarin enantiomers to HSA at 25° C. The equilibrium constants that were used for R- and S-warfarin were 2.6 (±0.1) × $10^5$ $M^{-1}$ and 3.4 (±0.1) × $10^5$ $M^{-1}$, respectively.

The accuracy of these free fractions was evaluated by comparing them with the predicted results for these samples. This was accomplished by using the known composition of these samples and equilibrium constants that have previously been determined for the binding of R- and S-warfarin to HSA under conditions similar to those used in this study (Loun, B.; Hage, D. S. Anal. Chem. 1994, 66, 3814.). It was assumed in these calculations that essentially all of the HSA was active; this was confirmed experimentally through the use of fluorescence and a solution-phase titration of the HSA with increasing concentrations of warfarin. For R-warfarin, it was predicted that approximately 10±2% of this drug would be in the free form at equilibrium for the given sample composition, while for S-warfarin a predicted free fraction of 7±1 was obtained. Both predicted results were within one standard deviation of the experimental free fractions, thus indicating that there was good agreement between these values.

An inherent assumption made throughout this project was that the anti-warfarin antibodies in the immunoaffinity column would be able to distinguish between the free warfarin in solution and its HSA-bound fraction. For this to be true, these antibodies would have to interact with regions in the structure of warfarin that were not exposed when this drug was complexed with HSA. The agreement between the actual and predicted results in Table 2 indicates that this was indeed the case. This specificity for the free versus bound fractions was not surprising in the case of R-warfarin, which is believed to interact deep within its binding site on HSA. But a similar specificity was noted for S-warfarin, which is thought to interact more with HSA's outer surface. This result indicates that it should be possible to use immunoaffinity chromatography to isolate the free fractions of drugs that have a variety of different orientations in their drug-protein complexes. However, as a precaution, it is still recommended that antibody specificity always be considered for any new compounds that are to be examined by this analytical technique.

EXAMPLE 4

Simulation of Warfarin Extraction and Dissociation

After the free fractions of R- and S-warfarin had been determined in test samples, a comparison was made between the accuracy of these values and the errors that had been anticipated due to the dissociation of bound warfarin during such measurements. For instance, the differences in the measured and predicted free fractions in Table 2 (+18% for R-warfarin and −16% for S-warfarin) were much smaller than the errors of 20–40% that were expected from FIG. 4 and related plots at comparable extraction times. It was suspected from this that these earlier graphs had overestimated the role played by dissociation effects during the isolation of free drug fractions by immunoaffinity chromatography.

A more complete picture of the immunoaffinity extraction process was obtained through the use of computer simulations. This was accomplished by developing a model which no longer made the same assumptions that were used in FIG. 4. For instance, this model allowed the free and dissociated warfarin to undergo a continuous (rather than instantaneous) extraction on the immunoaffinity microcolumn. It was also now possible to consider the use of a column with a finite binding capacity and samples in which any non-complexed warfarin could bind to HSA instead of the immobilized antibodies. This was accomplished by adapting a previous algorithm that has been used to study the adsorption of analytes to affinity supports, (Hage, D. S.; Walters, R. R. *J. Chromatogr.* 1988, 436, 111; Rollag, J. G.; Hage, D. S. *J. Chromatogr. A* 1998, 795, 185; and Hage, D. S.; Thomas, D. H.; Roy Chowdhuri, A.; Clarke, W. *Anal. Chem.* 1999, 71, 2965.) with the inclusion of a reversible solution-phase reaction between the injected drug and its binding proteins. Further details on this approach can be found in the Methods and Materials.

Figure 8:
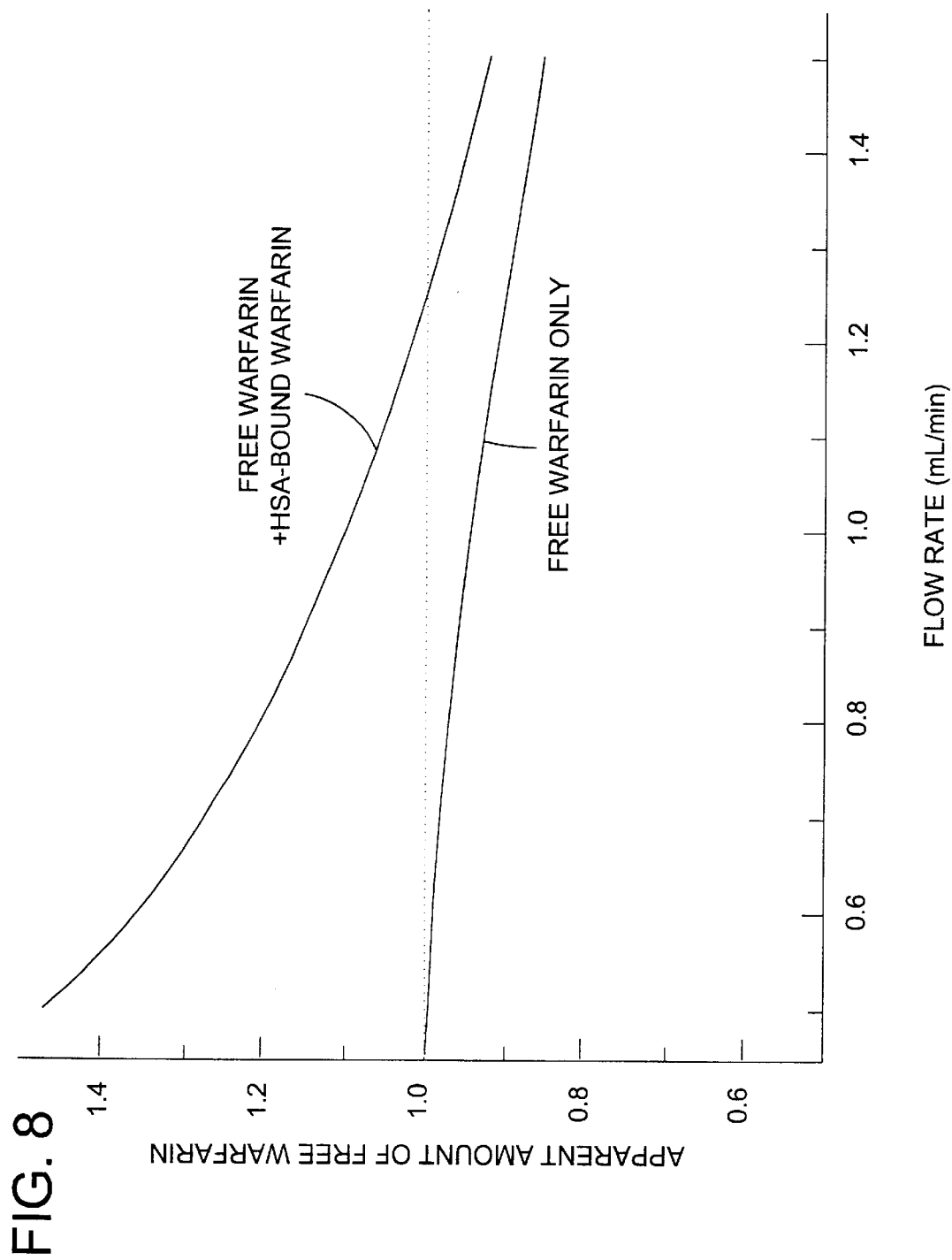
FIG. 8 depicts simulated extraction of free warfarin from a mixture of R-warfarin and HSA. The sample and column conditions used in generating this plot were the same as those that were present for the experimental results in FIG. 7. The solid bottom line indicates the relative amount of free warfarin that was extracted in the absence of HSA. The solid top line shows the amount of warfarin that was extracted from warfarin/HSA mixtures when the bound warfarin was allowed to dissociate from and rebind to HSA as the sample passed through the column. The dashed line is shown for reference and represents a case in which the amount of extracted warfarin was identical to the amount of free warfarin in the injected samples. These simulations were based on association and dissociation rate constants of $1 \times 10^5$ M$^{-1}$ S$^{-1}$ and 0.4 s$^{-1}$ for the interactions of R-warfarin with HSA at 25° C. The adsorption of warfarin to the immunoaffinity column was described by using a column binding capacity of $5 \times 10^{-11}$ mol and a second-order association rate constant of $1 \times 10^5$ M$^{-1}$ S$^{-1}$.

FIG. 8 shows the simulation results that were obtained for R-warfarin. Similar plots were generated for S-warfarin. The sample and column conditions that were used in these simulations were the same as those that were present in the experimental determination of the free warfarin fractions. The rate constant for adsorption of warfarin to the immobilized antibodies was estimated from the earlier studies that examined the extraction of R- and S-warfarin by the immunoaffinity column.

The lower plot in FIG. 8 shows how the extraction efficiency of warfarin was predicted to change as this drug was injected at various flow rates. This extraction had its highest efficiency at low flow rates and a decreasing efficiency at higher flow rates. This occurs because there is a smaller contact time between the sample and the immobilized antibodies as higher application flow rates are used.

The top plot in FIG. 8 shows how the relative concentration of extracted warfarin compared to the true free fraction in warfarin/HSA mixtures when the bound warfarin in these samples was allowed to undergo dissociation and rebinding to the HSA. As expected, higher flow rates and shorter column residence times resulted in less dissociation effects. This, in turn, allowed the concentration of extracted warfarin (free plus dissociated warfarin) to approach the concentration of free warfarin that was actually removed from the sample.

One observation that can be made by comparing the two plots in FIG. 8 is that there will be an optimum flow rate range over which the best estimates can be made of a drug's true free fraction. For instance, FIG. 8 shows that the extent of warfarin dissociation from HSA will be minimized by operating at high flow rates; however, this decreases extraction of the free warfarin fraction. Working at slower flow rates provides a better extraction efficiency but suffers from greater errors due to bound drug dissociation. It is only at intermediate flow rates that a balance is obtained between accuracy and extraction recovery. In this particular case, it was predicted that a flow rate range of roughly 0.9–1.6 mL/min was needed to obtain an error of ±15% or less in the measured free fractions. This compares well with the approximate errors of +18% and −16% that were estimated for R- and S-warfarin under these flow rate conditions.

Another observation that can be made from FIG. 8 is that the free fraction errors predicted by the simulations were less than those that were originally estimated through the use of simple drug-protein dissociation. For instance, it was determined from FIG. 4 that dissociation of S-warfarin from HSA would increase the measured free fraction of this drug by 25–30% at an extraction time of 180 ms. However, the more complete model used in the simulations indicated that a maximum error of only 15% would be expected.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method to determine the concentration of a free analyte fraction in a sample, the sample comprising a biological fluid having a bound analyte fraction and the free analyte fraction, the method comprising:
   (a) applying, the sample to an affinity column having an active layer which selectively binds free analyte relative to bound analyte wherein the active layer separates the free analyte fraction from the bound analyte fraction of the sample in the millisecond time domain;
   (b) detection of signal from the free analyte fraction separated from the sample; and
   (c) determining the concentration of free analyte present in the sample.

2. The method of claim 1 wherein the affinity column comprises an active layer, the active layer comprising support particles derivatized with a binding agent.

3. The method of claim 2 wherein the active layer is from about 10 microns to about 1.1 millimeters in length.

4. The method of claim 2 wherein the active layer is not less than 60 microns in length.

5. The method of claim 2 wherein the binding agent is selected from the group of agents consisting of antibodies, aptamers, antibody fragments, synthetic molecular imprints, antibody related molecules and recombinant proteins.

6. The method of claim 5 wherein the binding agent is antibodies.

7. The method of claim 6 wherein the binding agent has a high binding affinity for the free analyte fraction.

8. The method of claim 7 wherein the binding agent has a binding affinity for the free analyte fraction from about $10^2$ to about $10^6$ $M^{-1}$.

9. The method of claim 7 wherein the binding agent has a binding affinity for the free analyte fraction greater than about $10^6$ $M^{-1}$.

10. The method of claim 7 wherein the free analyte fraction is separated from the sample from about 1 to about 500 milliseconds after injection of the sample into the microcolumn.

11. The method of claim 10 wherein the free analyte fraction is separated from the sample from about 1 to about 100 milliseconds after injection of the sample into the microcolumn.

12. The method of claim 10 wherein the signal is detected from the free analyte fraction by an off-line method or an on-line method.

13. The method of claim 12 wherein the signal is detected by an on-line method with direct detection.

14. The method of claim 12 wherein the signal is detected by a method selected from the group consisting of immunoassay, mass spectrometry, gas chromatography, ultraviolet absorbance, fluorescence detectors, and electrochemical detectors.

15. A method to determine the concentration of a free analyte fraction in a sample, the sample comprising a bound analyte fraction and the free analyte fraction, the method comprising:

(a) applying the sample to an affinity column wherein the column separates the free analyte fraction from the sample in the millisecond time domain;

(b) detection of signal from the free analyte fraction separated from the sample; and (c) comparing the signal detected in (b) to a standard thereby determining the concentration of free analyte present in the sample.

16. The method of claim 12 wherein the active layer is introduced by a plurality of injections.

17. The method of claim 16 wherein the active layer is introduced by about 10 to about 100 injections.

18. The method of claim 17 wherein the active layer is introduced by about 30 to about 40 injections when the active layer is from about 100 to about 500 microns in length.

19. The method of claim 17 wherein the active layer is introduced by about 60 to about 80 injections when the active layer is from about 60 to about 100 microns in length.

20. The method of claim 17 wherein the support particles comprising the active layer are injected onto the column at a density of from about 0.1 to about 20 milligrams of support particle per milliliter of packing solvent.

21. The method of claim 16 wherein the biological fluid is selected from the group consisting of blood, plasma, urine, cerebrospinal fluid, a tissue sample, and intracellular fluid.

22. The method of claim 21 wherein the binding capacity of the active layer comprises a ratio of the number of active binding sites to amount of free analyte present in the sample between about 1:1 to about 10:1.

23. The method of claim 22 wherein the sample is injected onto the column at a flow rate of about 0.01 to about 9.0 milliliters per minute.

24. The method of claim 23 wherein the sample is injected onto the column at a pressure of about 100 to about 1500 psi.

* * * * *

UNITED STATES PATENT AND TRADEMARK OFFICE
CERTIFICATE OF CORRECTION

| | | |
|---|---|---|
| PATENT NO. | : 6,720,193 B2 | Page 1 of 1 |
| APPLICATION NO. | : 09/794857 | |
| DATED | : April 13, 2004 | |
| INVENTOR(S) | : David S. Hage and William A. Clarke | |

It is certified that error appears in the above-identified patent and that said Letters Patent is hereby corrected as shown below:

Column 1
Line 10, delete "5 R01".

Signed and Sealed this

Twentieth Day of May, 2008

JON W. DUDAS
*Director of the United States Patent and Trademark Office*